(12) United States Patent
Essinger et al.

(10) Patent No.: US 10,219,897 B2
(45) Date of Patent: Mar. 5, 2019

(54) STENTS, VALVED-STENTS AND METHODS AND SYSTEMS FOR DELIVERY THEREOF

(71) Applicant: Symetis SA, Ecublens (CH)

(72) Inventors: Jacques Essinger, St-Prex (CH); Serge Delaloye, Chamoson (CH); Jean-Luc Hefti, Cheseaux-Noreaz (CH); Stephane Delaloye, Bulach (CH)

(73) Assignee: SYMETIS SA, Ecublens (CH)

( * ) Notice: Subject to any disclaimer, the term of this patent is extended or adjusted under 35 U.S.C. 154(b) by 0 days.

(21) Appl. No.: 15/809,123

(22) Filed: Nov. 10, 2017

(65) Prior Publication Data

US 2018/0064533 A1 Mar. 8, 2018

Related U.S. Application Data

(63) Continuation of application No. 15/241,985, filed on Aug. 19, 2016, now Pat. No. 9,836,513, which is a continuation of application No. 14/158,509, filed on Jan. 17, 2014, now abandoned, which is a continuation of application No. 12/739,117, filed as application No. PCT/EP2008/064558 on Oct. 27, 2008, now Pat. No. 8,647,381.

(60) Provisional application No. 61/052,560, filed on May 12, 2008, provisional application No. 61/067,189, filed on Feb. 25, 2008, provisional application No. 61/000,587, filed on Oct. 25, 2007.

(51) Int. Cl.
*A61F 2/24* (2006.01)

(52) U.S. Cl.
CPC .............. *A61F 2/2418* (2013.01); *A61F 2/24* (2013.01); *A61F 2/2436* (2013.01); *A61F 2220/0075* (2013.01); *A61F 2230/005* (2013.01); *A61F 2230/0013* (2013.01); *A61F 2230/0054* (2013.01); *A61F 2230/0078* (2013.01); *A61F 2250/0098* (2013.01)

(58) Field of Classification Search
CPC ................................. A61F 2/24; A61F 2/2412
USPC .................................................. 623/2.11–2.19
See application file for complete search history.

(56) References Cited

U.S. PATENT DOCUMENTS 3,755,823 A 9/1973 Hancock
4,106,129 A 8/1978 Carpentier et al.
(Continued)

FOREIGN PATENT DOCUMENTS

AU 2006328896 A1 6/2007
AU 2007294199 A1 3/2008
(Continued)

OTHER PUBLICATIONS

Akins, et al., "Risk of Preoperative Valve Replacement for Failed Mitral and Aortic Bioprostheses", Ann Thorac Surg (1998), 65: 1545-52.
(Continued)

*Primary Examiner* — Suzette J Gherbi
(74) *Attorney, Agent, or Firm* — Seager, Tufte & Wickhem LLP

(57) ABSTRACT

Embodiments of the present disclosure are directed to stents, valved-stents, (e.g., single-stent-valves and double stent/valved-stent systems) and associated methods and systems for their delivery via minimally-invasive surgery. The stent component comprises a first stent section (102) a second stent section (104) a third stent section (106) and a fourth stent section (108).

17 Claims, 26 Drawing Sheets

(56) References Cited

U.S. PATENT DOCUMENTS

| | | |
|---|---|---|
| 4,470,157 A | 9/1984 | Love |
| 5,078,720 A | 1/1992 | Burton et al. |
| 5,163,955 A | 11/1992 | Love et al. |
| 5,192,301 A | 3/1993 | Kamiya et al. |
| 5,344,442 A | 9/1994 | Deac |
| 5,354,330 A | 10/1994 | Hanson et al. |
| 5,411,552 A | 5/1995 | Andersen et al. |
| 5,480,424 A | 1/1996 | Cox |
| 5,499,995 A | 3/1996 | Teirstein |
| 5,500,015 A | 3/1996 | Deac |
| 5,540,712 A | 7/1996 | Kleshinski et al. |
| 5,571,174 A | 11/1996 | Love et al. |
| 5,609,626 A | 3/1997 | Quijano et al. |
| 5,653,749 A | 8/1997 | Love et al. |
| 5,662,703 A | 9/1997 | Yurek et al. |
| 5,713,950 A | 2/1998 | Cox |
| 5,713,951 A | 2/1998 | Garrison et al. |
| 5,718,725 A | 2/1998 | Sterman et al. |
| 5,769,882 A | 6/1998 | Fogarty et al. |
| 5,797,960 A | 8/1998 | Stevens et al. |
| 5,807,327 A | 9/1998 | Green et al. |
| 5,817,126 A | 10/1998 | Imran |
| 5,823,956 A | 10/1998 | Roth et al. |
| 5,824,041 A | 10/1998 | Lenker et al. |
| 5,840,081 A | 11/1998 | Andersen et al. |
| 5,855,600 A | 1/1999 | Alt |
| 5,855,601 A | 1/1999 | Bessler et al. |
| 5,861,028 A | 1/1999 | Angell |
| 5,924,424 A | 7/1999 | Stevens et al. |
| 5,938,697 A | 8/1999 | Killion et al. |
| 5,957,949 A | 9/1999 | Leonhardt et al. |
| 5,976,174 A | 11/1999 | Ruiz |
| 5,980,533 A | 11/1999 | Holman |
| 6,029,671 A | 2/2000 | Stevens et al. |
| 6,083,257 A | 7/2000 | Taylor et al. |
| 6,102,944 A | 8/2000 | Huynh et al. |
| 6,110,201 A | 8/2000 | Quijano et al. |
| 6,168,614 B1 | 1/2001 | Andersen et al. |
| 6,171,335 B1 | 1/2001 | Wheatley et al. |
| 6,183,481 B1 | 2/2001 | Lee et al. |
| 6,196,230 B1 | 3/2001 | Hall et al. |
| 6,214,036 B1 | 4/2001 | Letendre et al. |
| 6,254,564 B1 | 7/2001 | Wilk et al. |
| 6,287,334 B1 | 9/2001 | Moll et al. |
| 6,287,339 B1 | 9/2001 | Vazquez et al. |
| 6,331,189 B1 | 12/2001 | Wolinsky et al. |
| 6,350,278 B1 | 2/2002 | Lenker et al. |
| 6,379,383 B1 | 4/2002 | Palmaz et al. |
| 6,401,720 B1 | 6/2002 | Stevens et al. |
| 6,406,493 B1 | 6/2002 | Tu et al. |
| 6,409,759 B1 | 6/2002 | Peredo |
| 6,454,799 B1 | 9/2002 | Schreck |
| 6,458,153 B1 | 10/2002 | Bailey et al. |
| 6,530,952 B2 | 3/2003 | Vesely |
| 6,533,807 B2 | 3/2003 | Wolinsky et al. |
| 6,537,310 B1 | 3/2003 | Palmaz et al. |
| 6,562,069 B2 | 5/2003 | Cai et al. |
| 6,569,196 B1 | 5/2003 | Vesely |
| 6,572,652 B2 | 6/2003 | Shaknovich |
| 6,582,462 B1 | 6/2003 | Andersen et al. |
| 6,589,279 B1 | 7/2003 | Anderson et al. |
| 6,613,079 B1 | 9/2003 | Wolinsky et al. |
| 6,635,085 B1 | 10/2003 | Caffey et al. |
| 6,652,555 B1 | 11/2003 | VanTassel et al. |
| 6,682,558 B2 | 1/2004 | Tu et al. |
| 6,682,559 B2 | 1/2004 | Myers et al. |
| 6,695,865 B2 | 2/2004 | Boyle et al. |
| 6,719,787 B2 | 4/2004 | Cox |
| 6,730,118 B2 | 5/2004 | Spenser et al. |
| 6,733,525 B2 | 5/2004 | Yang et al. |
| 6,736,827 B1 | 5/2004 | McAndrew et al. |
| 6,755,855 B2 | 6/2004 | Yurek et al. |
| 6,767,362 B2 | 7/2004 | Schreck |
| 6,790,229 B1 | 9/2004 | Berreklouw |
| 6,805,711 B2 | 10/2004 | Quijano et al. |
| 6,830,584 B1 | 12/2004 | Seguin |
| 6,830,585 B1 | 12/2004 | Artof et al. |
| 6,830,586 B2 | 12/2004 | Quijano et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,936,066 B2 | 8/2005 | Palmaz et al. |
| 6,942,682 B2 | 9/2005 | Vrba et al. |
| 7,018,406 B2 | 3/2006 | Seguin et al. |
| 7,025,773 B2 | 4/2006 | Gittings et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,141,064 B2 | 11/2006 | Scott et al. |
| 7,179,290 B2 | 2/2007 | Cao |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,217,287 B2 | 5/2007 | Wilson et al. |
| 7,252,682 B2 | 8/2007 | Seguin |
| 7,276,078 B2 | 10/2007 | Spenser et al. |
| 7,285,130 B2 | 10/2007 | Austin |
| 7,316,712 B2 | 1/2008 | Peredo |
| 7,318,278 B2 | 1/2008 | Zhang et al. |
| 7,320,704 B2 | 1/2008 | Lashinski et al. |
| 7,320,705 B2 | 1/2008 | Quintessenza |
| 7,329,278 B2 | 2/2008 | Seguin et al. |
| 7,329,279 B2 | 2/2008 | Haug et al. |
| 7,331,991 B2 | 2/2008 | Kheradvar et al. |
| 7,331,993 B2 | 2/2008 | White |
| 7,338,484 B2 | 3/2008 | Schoon et al. |
| 7,361,189 B2 | 4/2008 | Case et al. |
| 7,371,258 B2 | 5/2008 | Woo et al. |
| 7,374,571 B2 | 5/2008 | Pease et al. |
| 7,377,938 B2 | 5/2008 | Sarac et al. |
| 7,381,218 B2 | 6/2008 | Schreck |
| 7,381,219 B2 | 6/2008 | Salahieh et al. |
| 7,393,358 B2 | 7/2008 | Malewicz |
| 7,393,360 B2 | 7/2008 | Spenser et al. |
| 7,399,315 B2 | 7/2008 | Iobbi |
| 7,402,171 B2 | 7/2008 | Osborne et al. |
| 7,410,499 B2 | 8/2008 | Bicer |
| 7,416,530 B2 | 8/2008 | Turner et al. |
| 7,422,603 B2 | 9/2008 | Lane |
| 7,431,733 B2 | 10/2008 | Knight |
| 7,435,257 B2 | 10/2008 | Lashinski et al. |
| 7,445,632 B2 | 11/2008 | McGuckin, Jr. et al. |
| 7,455,689 B2 | 11/2008 | Johnson |
| 7,470,284 B2 | 12/2008 | Lambrecht et al. |
| 7,470,285 B2 | 12/2008 | Nugent et al. |
| 7,473,275 B2 | 1/2009 | Marquez |
| 7,481,838 B2 | 1/2009 | Carpentier et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,510,572 B2 | 3/2009 | Gabbay |
| 7,510,575 B2 | 3/2009 | Spenser et al. |
| 7,513,909 B2 | 4/2009 | Lane et al. |
| 7,534,261 B2 | 5/2009 | Friedman |
| 7,556,646 B2 | 7/2009 | Yang et al. |
| 7,578,828 B2 | 8/2009 | Gittings et al. |
| 7,585,321 B2 | 9/2009 | Cribier |
| 7,591,848 B2 | 9/2009 | Allen |
| 7,618,446 B2 | 11/2009 | Andersen et al. |
| 7,625,403 B2 | 12/2009 | Krivoruchko |
| 7,632,296 B2 | 12/2009 | Malewicz |
| 7,682,390 B2 | 3/2010 | Seguin |
| 7,780,726 B2 | 8/2010 | Seguin |
| 7,846,203 B2 | 12/2010 | Cribier |
| 7,846,204 B2 | 12/2010 | Letac et al. |
| 7,896,915 B2 | 3/2011 | Guyenot et al. |
| 7,914,575 B2 | 3/2011 | Guyenot et al. |
| 7,947,075 B2 | 5/2011 | Goetz et al. |
| 7,959,672 B2 | 6/2011 | Salahieh et al. |
| 8,002,825 B2 | 8/2011 | Letac et al. |
| 8,052,749 B2 | 11/2011 | Salahieh et al. |
| 8,057,540 B2 | 11/2011 | Letac et al. |
| 8,092,518 B2 | 1/2012 | Schreck |

(56) References Cited

U.S. PATENT DOCUMENTS

| | | |
|---|---|---|
| 8,092,520 B2 | 1/2012 | Quadri |
| 8,603,159 B2 | 12/2013 | Seguin et al. |
| 8,628,571 B1 | 1/2014 | Hacohen et al. |
| 8,647,381 B2 | 2/2014 | Essinger et al. |
| 2001/0007956 A1 | 7/2001 | Letac et al. |
| 2003/0023300 A1 | 1/2003 | Bailey et al. |
| 2003/0028213 A1 | 2/2003 | Thill et al. |
| 2003/0040792 A1 | 2/2003 | Gabbay |
| 2003/0042186 A1 | 3/2003 | Boyle |
| 2003/0109924 A1 | 6/2003 | Cribier |
| 2004/0019374 A1 | 1/2004 | Hojeibane et al. |
| 2004/0044361 A1 | 3/2004 | Frazier et al. |
| 2004/0044400 A1 | 3/2004 | Cheng et al. |
| 2004/0093060 A1 | 5/2004 | Seguin et al. |
| 2004/0093063 A1 | 5/2004 | Wright et al. |
| 2004/0106976 A1 | 6/2004 | Bailey et al. |
| 2004/0186563 A1 | 9/2004 | Lobbi |
| 2004/0210304 A1 | 10/2004 | Seguin et al. |
| 2004/0254594 A1 | 12/2004 | Alfaro |
| 2004/0260389 A1 | 12/2004 | Case et al. |
| 2005/0043759 A1 | 2/2005 | Chanduszko |
| 2005/0043790 A1 | 2/2005 | Seguin |
| 2005/0070794 A1 | 3/2005 | Deal et al. |
| 2005/0113910 A1 | 5/2005 | Paniagua et al. |
| 2005/0137681 A1 | 6/2005 | Shoemaker et al. |
| 2005/0137688 A1 | 6/2005 | Salahieh et al. |
| 2005/0137696 A1 | 6/2005 | Salahieh et al. |
| 2005/0137702 A1 | 6/2005 | Haug et al. |
| 2005/0182483 A1 | 8/2005 | Osborne et al. |
| 2005/0267523 A1 | 12/2005 | Devellian et al. |
| 2005/0283231 A1 | 12/2005 | Haug et al. |
| 2005/0288706 A1 | 12/2005 | Widomski et al. |
| 2006/0004442 A1 | 1/2006 | Spenser et al. |
| 2006/0122692 A1 | 6/2006 | Gilad et al. |
| 2006/0149360 A1 | 7/2006 | Schwammenthal et al. |
| 2006/0161248 A1 | 7/2006 | Case et al. |
| 2006/0195180 A1 | 8/2006 | Kheradvar et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0287717 A1 | 12/2006 | Rowe et al. |
| 2007/0060998 A1 | 3/2007 | Butterwick et al. |
| 2007/0061002 A1 | 3/2007 | Paul et al. |
| 2007/0142907 A1 | 6/2007 | Moaddeb et al. |
| 2007/0179600 A1 | 8/2007 | Vardi |
| 2007/0198097 A1 | 8/2007 | Zegdi |
| 2007/0213813 A1 | 9/2007 | Von Segesser et al. |
| 2007/0239265 A1 | 10/2007 | Birdsall |
| 2007/0239269 A1 | 10/2007 | Dolan et al. |
| 2007/0244543 A1 | 10/2007 | Mitchell |
| 2007/0282436 A1 | 12/2007 | Pinchuk |
| 2008/0071361 A1 | 3/2008 | Tuval et al. |
| 2008/0071362 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0125859 A1 | 5/2008 | Salahieh et al. |
| 2008/0140189 A1 | 6/2008 | Nguyen et al. |
| 2008/0161909 A1 | 7/2008 | Kheradvar et al. |
| 2008/0177381 A1 | 7/2008 | Navia et al. |
| 2008/0195199 A1 | 8/2008 | Kheradvar et al. |
| 2008/0208327 A1 | 8/2008 | Rowe |
| 2008/0228263 A1 | 9/2008 | Ryan |
| 2008/0234814 A1 | 9/2008 | Salahieh et al. |
| 2008/0255660 A1 | 10/2008 | Guyenot et al. |
| 2008/0269878 A1 | 10/2008 | Iobbi |
| 2008/0275550 A1 | 11/2008 | Kheradvar et al. |
| 2009/0005863 A1 | 1/2009 | Goetz et al. |
| 2009/0076598 A1* | 3/2009 | Salahieh et al. ......... 623/2.11 |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0276040 A1 | 11/2009 | Rowe et al. |
| 2009/0287299 A1 | 11/2009 | Tabor et al. |
| 2010/0168839 A1 | 7/2010 | Braido et al. |
| 2011/0022157 A1 | 1/2011 | Essinger et al. |
| 2011/0040374 A1 | 2/2011 | Goetz et al. |
| 2011/0224780 A1 | 9/2011 | Tabor et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123529 A1 | 5/2012 | Levi et al. |
| 2012/0172982 A1 | 7/2012 | Stacchino et al. |
| 2012/0303116 A1 | 11/2012 | Gorman, III et al. |

FOREIGN PATENT DOCUMENTS

| | | |
|---|---|---|
| AU | 2009200985 A1 | 4/2009 |
| CA | 2634358 A1 | 6/2007 |
| CA | 2657839 A1 | 3/2008 |
| CA | 2659690 A1 | 3/2008 |
| DE | 20003874 U1 | 5/2000 |
| DE | 19857887 A1 | 7/2000 |
| DE | 102005003632 A1 | 8/2006 |
| DE | 202007005491 U1 | 6/2007 |
| EP | 0592410 | 4/1994 |
| EP | 0657147 A2 | 6/1995 |
| EP | 0696447 A2 | 2/1996 |
| EP | 0943302 A2 | 9/1999 |
| EP | 1093771 A2 | 4/2001 |
| EP | 1262201 A1 | 12/2002 |
| EP | 1264582 A2 | 12/2002 |
| EP | 1267753 B1 | 10/2005 |
| EP | 1598031 A2 | 11/2005 |
| EP | 1251797 B1 | 11/2007 |
| EP | 1968491 A2 | 9/2008 |
| EP | 2033593 A1 | 3/2009 |
| EP | 2047824 A1 | 4/2009 |
| EP | 2059192 A1 | 5/2009 |
| EP | 2074964 A1 | 7/2009 |
| FR | 2874812 A1 | 3/2006 |
| WO | 1998029057 A1 | 7/1998 |
| WO | 2000028922 A1 | 5/2000 |
| WO | 2000047139 A1 | 8/2000 |
| WO | 2000053122 A1 | 9/2000 |
| WO | 2001049213 A2 | 7/2001 |
| WO | 2001062189 A1 | 8/2001 |
| WO | 2002067782 A2 | 9/2002 |
| WO | 2002076349 A1 | 10/2002 |
| WO | 2003003949 A2 | 1/2003 |
| WO | 2003047468 A1 | 6/2003 |
| WO | 2003063729 A2 | 8/2003 |
| WO | 2005070343 A1 | 8/2005 |
| WO | 2006058163 A2 | 6/2006 |
| WO | 2006068944 A2 | 6/2006 |
| WO | 2006076890 A1 | 7/2006 |
| WO | 2006083763 A1 | 8/2006 |
| WO | 2006086135 A2 | 8/2006 |
| WO | 2006086736 A2 | 8/2006 |
| WO | 2006127765 A1 | 11/2006 |
| WO | 2005102015 A2 | 4/2007 |
| WO | 2007054015 A1 | 5/2007 |
| WO | 2007071436 A2 | 6/2007 |
| WO | 2008028569 A1 | 3/2008 |
| WO | 2009029199 A1 | 3/2009 |
| WO | 2009042196 A2 | 4/2009 |
| WO | 2009045331 A1 | 4/2009 |
| WO | 2009045334 A1 | 4/2009 |
| WO | 2009045338 A1 | 4/2009 |
| WO | 2009053497 A1 | 4/2009 |
| WO | 2009061389 A2 | 5/2009 |
| WO | 2009091509 A1 | 7/2009 |
| WO | 2010045238 A2 | 4/2010 |
| WO | 2010045297 A2 | 4/2010 |
| WO | 2010049160 A1 | 5/2010 |
| WO | 2010083558 A1 | 7/2010 |
| WO | 2010098857 A1 | 9/2010 |
| WO | 2011051043 A1 | 5/2011 |
| WO | 2011057087 A1 | 5/2011 |
| WO | 2013033791 A1 | 3/2013 |
| WO | 2013134214 A1 | 9/2013 |
| WO | 2014072439 A1 | 5/2014 |

(56) References Cited

FOREIGN PATENT DOCUMENTS

OTHER PUBLICATIONS

Australian Examination Report, Application No. AU 2009200985, dated Mar. 4, 2010.
Dewey et al., "Transapical Aortic Valve Implantation: an Animal Feasibility Study", The annals of thoracic surgery, (2006): 82 pp. 110-116.
European Examination Report, Application No. EP07818037.9, dated Aug. 11, 2009.
European Search Report, EP09154935.2, dated May 29, 2009.
Examination Report, Application No. EP06841127.1, dated Feb. 6, 2009.
Examination Search Report issued by Canadian Intellectual Property Office dated Oct. 30, 2014 for Canadian Application No. 2,703,665, filed Apr. 21, 2010.
Huber, et al., Direct-Access Valve Replacement: A Novel Approach for Off-Pump Valve Implantation Using Valved Stents; Journal of the American College of Cardiology, vol. 46, No. 2; 2005.
International Preliminary Report on Patentability, Application No. PCT/EP2006/012455, dated Jun. 24, 2008.
International Preliminary Report on Patentability, Application No. PCT/EP2007/07413, dated Mar. 10, 2009.
International Search Report for International Application No. PCT/EP2008/064558, date of completion of report, Mar. 18, 2009 and Written Opinion of the International Searching Authority for International Application No. PCT/EP2008/064558.
IPRP for PCT/EP2007/007413, issued Mar. 10, 2009.
IPRP for PCT/EP2010/057798, mailed Dec. 6, 2011.
IPRP for PCT/IB2008/002180, issued Feb. 24, 2010.
IPRP issued Mar. 26, 2013 for PCT/EP2011/066677.
IPRP issued May 8, 2012 for PCT/EP2010/063306.
ISR & WO for PCT/IB2008/002180, mailed Apr. 15, 2009.
ISR for PCT/EP2007/007413, mailed Jan. 28, 2008.
ISR for PCT/EP2010/057798, mailed Dec. 9, 2010.
ISR mailed Apr. 17, 2014 for PCT/EP2013/073318.
ISR mailed Feb. 17, 2012 for PCT/EP2011/066677.
Lichtenstein, et al., Transapical Transcatheter Aortic Valve Implantation in Humans: Initial Clinical Experience; Circulation, American Heart Association, vol. 114; 2006.
Ma et al., "Double-crowned valved stents for off-pump mitral valve replacement", European Journal of Cardio-Thoracic Surgery (2005), 28:194-199.
Mack, M. J., "Minimally invasive cardiac surgery", Surg Endosc, (2006) 20:S488-S492, Apr. 24, 2006.
Moazami, et al., Transluminal Aortic Valve Placement: A Feasibility Study with a Newly Designed Collapsible Aortic Valve; ASAIO Journal, vol. 42; 1996.
Office Action issued by Canadian Intellectual Property Office dated Nov. 7, 2014 for Canadian Application No. 2,703,665, filed Apr. 21, 2010.
Partial International Search Report for International Application No. PCT/EP2014/055044, filed Mar. 13, 2014.
Pawelec-Wojtalk, "Closure of Left Ventricle Perforation with the Use of Muscular VSD Occluder", European Journal of Cardio-Thoracic Surgery (2005), 27:714-716.
Walther et al., "Transapical approach for sutureless stent-fixed aortic valve implantation: experimental results", European Journal of Cardio-thoriacic Surgery 29(2006), p. 703-708.
Webb, et al., Percutaneous Aortic Valve Implantation Retrograde from the Femoral Artery; Circulation, American Heart Association, vol. 113; 2006.
Weerasinghe et al., "First Redo Heart Valve Replacement: A 10-Year Analysis", Circulation (1999), 99:655-658.
WO and ISR for PCT/EP2010/063306, mailed Nov. 17, 2010.

\* cited by examiner

Stabilization arches independent of valve fixation arches

Connections

Stabilization arches with gradual stiffness change and connected to valve fixation arches

STENTS, VALVED-STENTS AND METHODS AND SYSTEMS FOR DELIVERY THEREOF

CROSS-REFERENCE TO RELATED APPLICATIONS

The present application is a continuation of U.S. application Ser. No. 15/241,985, filed Aug. 19, 2016, which is a continuation of U.S. application Ser. No. 14/158,509, filed Jan. 17, 2014, continuation of U.S. application Ser. No. 12/739,117, filed Apr. 21, 2010, which is a 35 U.S.C. § 371 national stage entry of PCT/EP2008/064558 which has an international filing date of Oct. 27, 2008 and claims priority to U.S. Provisional Application Nos. 61/000,587 filed Oct. 25, 2007; 61/067,189 filed Feb. 25, 2008, and 61/052,560, filed May 12, 2008. The present application incorporates herein by reference the disclosures of each of the above-referenced applications in their entireties.

FIELD OF THE DISCLOSURE

Embodiments of the present disclosure are directed to systems, methods, and devices for cardiac valve replacement in mammalian hearts.

BACKGROUND OF THE DISCLOSURE

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to establish a Jess invasive cardiac valve replacement procedure, by delivering and implanting a cardiac replacement valve via a catheter percutaneously (i.e., through the skin) via either a transvascular approach—delivering the new valve through the femoral artery, or by transapical route, where the replacement valve is delivered between ribs and directly through the wall of the heart to the implantation site.

While Jess invasive and arguably less complicated, percutaneous heart valve replacement therapies (PHVT) still have various shortcomings, including the inability for a surgeon to ensure proper positioning and stability of the replacement valve within the patient's body. Specifically, if the replacement valve is not placed in the proper position relative to the implantation site, it can lead to poor functioning of the valve. For example, in an aortic valve replacement, if the replacement valve is placed too high, it can lead to valve regurgitation, instability, valve prolapse and/or coronary occlusion. If the valve is placed too low, it can also lead to regurgitation and mitral valve interaction.

To address such risks, recapture procedures and systems have been developed. For example, such a system is disclosed in U.S. publication no. 20050137688 and U.S. Pat. No. 5,957,949, each disclosure of which is herein incorporated by reference. While such systems may address the problem of improper placement, they are somewhat complicated, requiring the use of wires which are removable attached to an end of the stent to pull the stent back into the delivery catheter.

Throughout this description, including the foregoing description of related art, any and all publicly available documents described herein, including any and all U. S. patents, are specifically incorporated by reference herein in their entirety. The foregoing description of related art is not intended in any way as an admission that any of the documents described therein, including pending United States patent applications, are prior art to embodiments according to the present disclosure. Moreover, the description herein of any disadvantages associated with the described products, methods, and/or apparatus, is not intended to limit inventions disclosed herein. Indeed, aspects of the disclosed embodiments may include certain features of the described products, methods, and/or apparatus without suffering from their described disadvantages.

SUMMARY OF THE DISCLOSURE

In some embodiments, a replacement valve for use within a human body is provided, where the replacement valve includes a valve component and a stent component (the replacement valve also being referred to as a valved-stentor a stent valve, and may be used interchangeably with replacement valve throughout the disclosure). The stent component defines a first (e.g., proximal) end and a second (e.g., distal) end and may include a plurality of stent section, and in some embodiments, at least four stent sections. The proximal end P of the stent component may be described as the end of the stent component/replacement valve which ultimately is positioned adjacent and/or within the left ventricle. Alternatively, the proximal end P of the stent component may be described as the end having anchoring elements for attachment to the delivery catheter (e.g., attachment end in a transapical delivery system). The distal end D of the stent component may be described as the end of the replacement valve/stent component which ultimately is positioned adjacent and/or near the ascending aorta, when, for example, the delivery catheter is advanced toward/into the ascending aorta in a transapical delivery system. According to preferred embodiments of the disclosure, the replacement valves according to at least some embodiments are released distal-to-proximal, that is, the end of the stent (replacement valve) which ultimately is positioned within/near/adjacent the aorta is released first, and the end of the stent (replacement valve) which ultimate is positioned within/near/adjacent the ventricle is released last. Such a delivery, according to preferred embodiments, is via a transapical approach, or through the heart muscle (as opposed to being delivered transvascularly). While preferred embodiments disclosed herein are described as being delivered through a direct heart access approach (e.g., transapical approach using transapical/direct access delivery systems), some embodiments of the present invention may be delivered transvascularly.

The first stent section may define an at least partly conical body and the first end of the stent component. The conical body of the first stent section may slope outwardly in the direction of the first end. In some embodiments, the first stent section may include at least one attachment element for removable attachment to a delivery device.

The second stent section may be in communication with the first stent section and may define an at least partly conical body. The conical body of the second stent section may slope outwardly in the direction of the second end.

The third stent section may be in communication with the second stent section and may define an at least partially cylindrical body. The third stent section may be configured to house at least a portion of the valve component. The third stent section may include a plurality of arches for fixation to a corresponding plurality of commissures of the valve component.

The fourth stent section may be in communication with the third stent section and may define the second end. The fourth stent section may further define an at least partly conical body, which may slope outwardly in the direction of the second end. The fourth stent section may include a plurality of arches larger than, but aligned with, the plurality of arches included in the third stent section.

The four stent sections may be formed, for example, by laser cutting a tube or single sheet of material (e.g., nitinol). For example, the stent may be cut from a tube and then step-by-step expanded up to its final diameter by heat treatment on a mandrel. As another example, the stent may be cut from a single sheet of material, and then subsequently rolled and welded to the desired diameter.

In some embodiments of the present disclosure, a stent component may be provided that includes a central, longitudinal axis and at least one attachment element for removable attachment to a delivery device. The at least one attachment element may be formed generally in the shape of a hook extending inwardly towards the central, longitudinal axis. The delivery device may include a stent holder comprising a groove for receiving the attachment element of the stent component, wherein release of the stent-valve from the stent holder may be facilitated by rotation of the stent holder relative to the attachment element.

In still other embodiments of the present disclosure, a replacement valve for use within a human body is provided that includes a valve component, a stent component for housing the valve component, and at least two skirts (e.g., polyester (PET) skirts). An inner skirt may be provided that covers at least a portion (e.g., all) of an outer surface of the valve component, where the inner skirt may be sutured to at least the inflow tract of the valve component and to an inner surface of the stent. An outer skirt may also be provided that is sutured onto an outer surface of the stent.

Some embodiments of the present disclosure provide a cardiac stent-valve delivery system that includes an inner assembly and an outer assembly. The inner assembly may include a guide wire lumen (e.g., polymeric tubing) and a stent holder for removable attachment to a stent-valve. The outer assembly may include a sheath. The imler member and the outer member may be co-axially positioned and slidable relative to one another in order to transition from a closed position to an open position, such that in the closed position the sheath encompasses the stent-valve still attached to the stent holder and thus constrains expansion of the stent-valve. In the open position, the outer sheath may not constrain expansion of the stent-valve and thus the stent-valve may detach from the stent holder and expand to a fully expanded configuration.

In some embodiments, the inner assembly of the delivery device may include a fluoroscopic marker fixed to the guide wire lumen distal of the stent holder.

In some embodiments, the diameter of the outer assembly of the delivery device varies over its longitudinal axis.

In still other embodiments, the delivery system comprises a rigid (e.g., stainless steel) shaft in communication with a proximal end of the guide wire lumen.

In some embodiments, the delivery system comprises a luer c01mector in communication with the rigid shaft.

In some embodiments of the present disclosure, a method is provided for replacing an aortic valve within a human body. A stent-valve may be covered with a sheath in order to maintain the stent-valve in a collapsed configuration. The stent-valve may then may be inserted in the collapsed configuration into the human body without contacting the ascending aorta or aortic arch. The stent-valve may be partially expanded by sliding the sheath towards the left ventricle of the heart. This sliding of the sheath towards the left ventricle may cause expansion of a distal end of the stent-valve while the proximal end of the stent-valve remains constrained by the sheath. The sheath may be further slid towards the left ventricle of the heart in order to cause full expansion of the stent-valve. In some embodiments, the stent-valve may be recaptured prior to its full expansion by sliding the sheath in the opposite direction.

In some embodiments, a method for cardiac valve replacement is provided that includes releasing a distal end of a stent-valve from a sheath, where the distal end includes a radiopaque marker positioned thereon. The stent-valve is rotated, if necessary, to orient the stent-valve appropriately with respect to the coronary arteries (e.g., to prevent the commissures from facing the coronary arteries). Arches of the stent-valve are released from the sheath, in order to cause the arches to contact the aorta. A first conical crown of the stent-valve is released from the sheath, in order to cause the first conical crown to contact the native valve leaflets. A second crown of the stent-valve is released from the sheath, in order to cause the second crown to contact an annulus/inflow tract. The second crown may be the proximal section of the stent-valve such that releasing the second crown causes the stent-valve to be fully released from the sheath.

BRIEF DESCRIPTION OF THE DRAWINGS

For a better understanding of the embodiments of the present disclosure, reference is made to the following description, taken in conjunction with the accompanying drawings, in which like reference characters refer to like parts throughout, and in which.

DETAILED DESCRIPTION

Figure 1A:
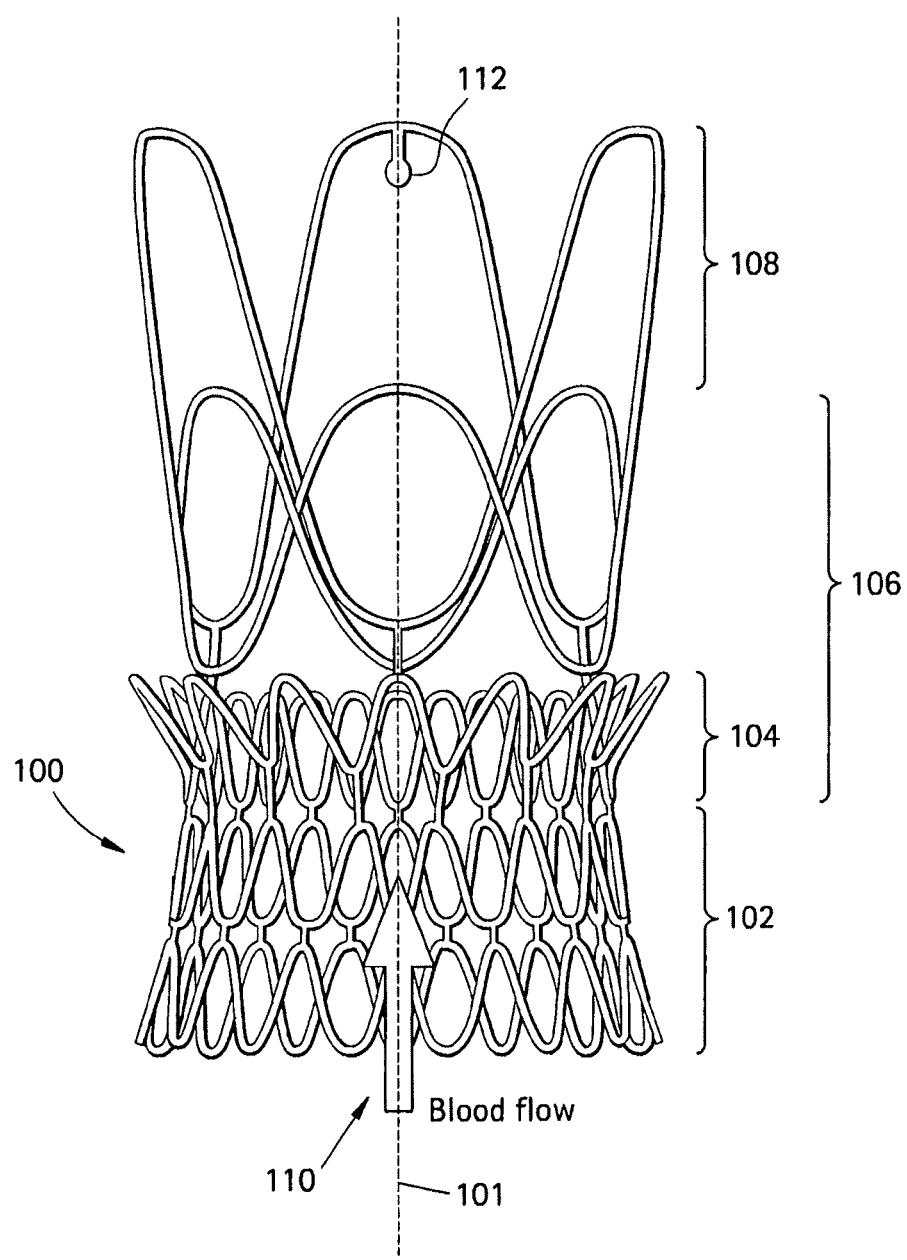
FIG. 1A is a side view of a stent component configured for distal-to-proximal expansion according to some embodiments of the present disclosure.

Some embodiments of the present disclosure are directed to systems, methods, and devices for cardiac valve replacement. For example, such methods, systems, and devices may be applicable to the full range of cardiac-valve therapies including, for example, replacement of failed aortic, mitral, tricuspid, and pulmonary valves. Some embodiments may facilitate a surgical approach on a beating heart without the need for an open-chest cavity and heart-lung bypass. This minimally-invasive surgical approach may reduce the risks associated with replacing a failed native valve in the first instance, as well as the risks associated with secondary or subsequent surgeries to replace failed artificial (e.g., biological or synthetic) valves.

Stents, Stent-Valves/Valved-Stents

Some embodiments of the present disclosure relate to stents and stent-valves or valved-stents. Valved-stents according to some embodiments of the present disclosure may include a valve component and at least one stent component (e.g., a single-stent-valve or a double-stent-valve). The valve component may include a biological valve (e.g., bovine harvested valve), a synthetic valve (e.g., either synthetic valve leaflet material and/or a mechanical valve assembly), any other suitable material(s). The stent and valve components according to some embodiments may be capable of at least two configurations: a collapsed or contracted configuration (e.g., during delivery) and an expanded configuration (e.g., after implantation).

According to some embodiments, the valved-stent or stent-valves of the present disclosure may be used as replacement heart valves and may be used in methods for replacing diseased or damaged heart valves. Heart valves are passive structures that simply open and close in response to differential pressures on either side of the particular valve. Heart valve comprise moveable "leaflets" that open and close in response to differential pressures on either side of the valve's leaflets. The mitral valve has two leaflets and the tricuspid valve has three. The aortic and pulmonary valves are referred to as "semilunar valves" due to the unique appearance of their leaflets or "cusps" and are shaped somewhat like a half-moon. The aortic and pulmonary valves each have three cusps.

The valve component is preferably designed to be flexible, compressible, host-compatible, and non-thrombogenic. The valve component can be made from various materials, for example, fresh, cryopreserved or glutaraldehyde fixed allografts or xenografts. Synthetic biocompatible materials such as polytetrafluoroethylene, polyester, polyurethane, nitinol or other alloy/metal foil sheet material and the like may be used. The preferred material for the valve component is mammal pericardium tissue, particularly juvenile-age animal pericardium tissue.

The valve component can be any replacement heart valve known or used and cardiac replacement valves. Replacement heart valves arc generally categorized into one of three categories: artificial mechanical valves; transplanted valves; and tissue valves. Mechanical valves are typically constructed from nonbiological materials such as plastics, metals, and other artificial materials. Transplanted valves are natural valves taken from cadavers. These valves are typically removed and frozen in liquid nitrogen, and are stored for later use. They are typically fixed in glutaraldehyde to eliminate antigenicity. Artificial tissue valves are valves constructed from animal tissue, such as bovine or porcine tissue. Efforts have also been made at using tissue from the patient for which the valve will be constructed. Such regenerative valves may also me used in combination with the stent components described herein. The choice of which type of replacement heart valves are generally based on the following considerations: hemodynamic performance, thrombogenicity, durability, and ease of surgical implantation.

Most tissue valves are constructed by sewing the leaflets of pig aortic valves to a stent to hold the leaflets in proper position, or by constructing valve leaflets from the pericardial sac of cows or pigs and sewing them to a stent. See e.g., U.S. Patent Publication No. 2005/0113910, the disclosure of which is herein incorporated by reference in its entirety. Methods of creating artificial tissue valves is described in U.S. Pat. Nos. 5,163,955, 5,571,174, and 5,653,749, the disclosures of which are herein incorporated by reference in their entireties.

According to some embodiment, the valve component is preferably attached to the inner channel of the stent member. This may be accomplished using any means known in the art. Preferably, the valve component is preferably attached to the inner channel of the stent member by suture or stitch, for example, by suturing the outer surface of the valve component pericardium material to the stent member. Preferably, the third stent section may be configured to house at least a portion of the valve component. Other fixation schemes can also be utilized. The attachment position of the valve is preferably closer to the proximal end of the stent chosen with the understanding that the annulus of the valve will preferably engage the outer surface of the stent at the groove (see FIG. 15D; 1560) created at the junction between the first and second sections of the stent component.

The stent component defines a first (e.g., proximal) end and a second (e.g., distal) end and includes at least four stent sections: a proximal conically shaped first section; a conically shaped second section; an optional cylindrically shaped third section; and a distal conically shaped forth section.

The first stent section may define an at least partly conical body and the first end of the stent component. The conical body of the first stent section may slope outwardly in the direction of the first end. For example, FIG. 2 shows a conically shaped first section 202 with an anchoring crown towards the ascending aorta. In some embodiments, the first stent section may include at least one attachment element for removable attachment to a delivery device.

The second stent section may be in communication with the first stent section and may define an at least partly conical body. The conical body of the second stent section may slope outwardly in the direction of the second end. For example, FIG. 2 shows a conically shaped second section 204 with an anchoring crown towards the left ventricle, or in the direction of blood flow (see e.g., FIG. 1).

Figure 10:
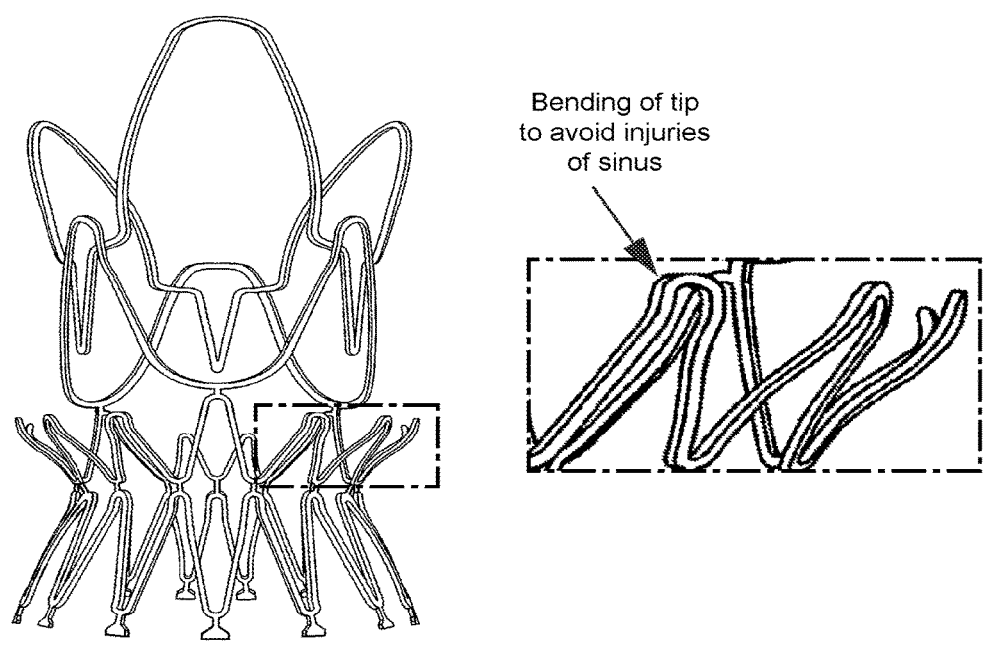
FIG. 10 shows the tip of the elements forming the anchoring crown, which may be bent towards the longitudinal axis of the stent thereby avoiding potential injury, such as injury to the sinus of vasalva during implantation of the device.

The radial force of this section may be increased by adjusting the length and angle (i.e., increased length HI and angle a1; see FIG. 5) of the stent struts to reduce the risk of migration towards the left ventricle. In some embodiments, the tip of the elements forming the anchoring crown may be bent towards the longitudinal axis of the stent thereby avoiding potential injury of the sinus of vasalva (see e.g., FIG. 10).

The third stent section may be in communication with the second stent section and may define an at least partially cylindrical body. The third stent section may be configured to house at least a portion of the valve component. The third stent section may include a plurality of arches for fixation to a corresponding plurality of commissures of the valve component. For example, FIG. 2 shows a cylindrical third section 206 which acts as a reinforcement crown.

Figure 11A:
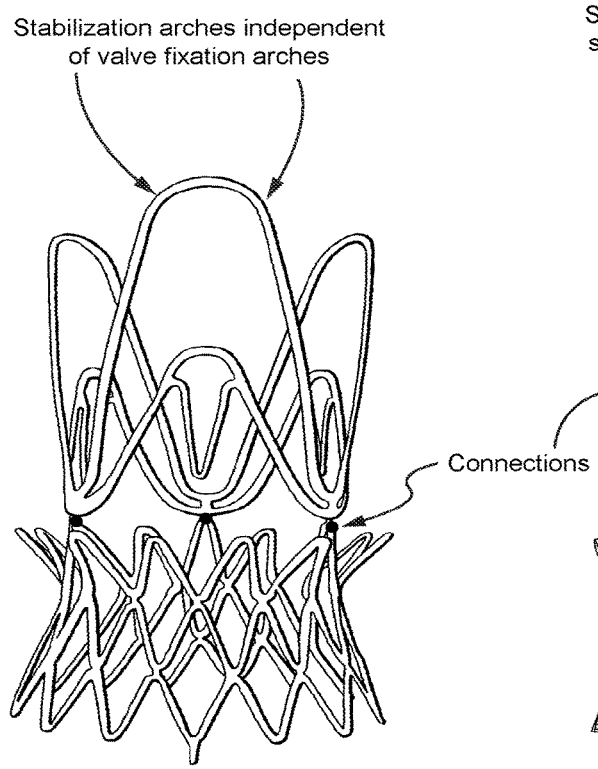
FIG. 11A shows an embodiment of the present disclosure, wherein the stabilization arches are designed to be independent of the valve fixation devices.
Figure 11B:
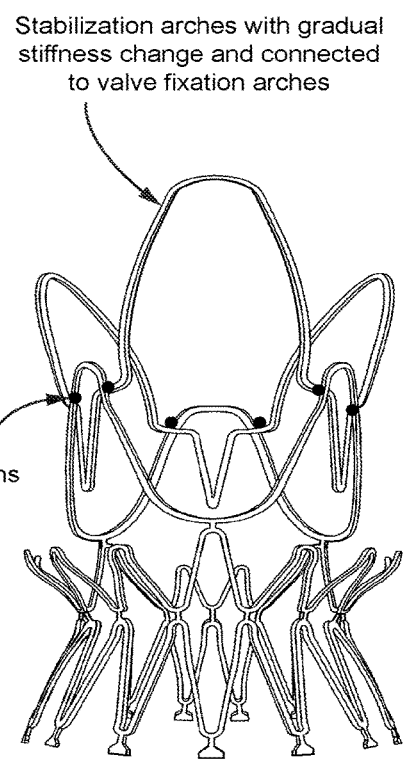
FIG. 11B shows an embodiment of the present disclosure, wherein the stabilization arches are designed with gradual stiffness change and connected to valve fixation arches.

The free area between the three valve fixation arches may be adjusted (i.e., increased or decreased) to improve the blood flow to the coronary arteries. This section of the stent may be attached to the previous anchoring crown (conically shaped section no 2) at three positions (see e.g., FIG. 11). This may allow for the out of plane bending of the elements of the section no 2 to form the conical shape.

The fourth stent section may be in communication with the third stent section and may define the second end. The fourth stent section may further define an at least partly conical body, which may slope outwardly in the direction of the second end. The fourth stent section may include a plurality of arches larger than, but aligned axially and/or circumferentially with, the plurality of arches included in the third stent section.

Stabilization arches may be provided within the ascending aorta that work independently of the valve fixation arches. Variations of the ascending aorta diameter may therefore have no impact on the valve fixation arches and thus on the valve haemodynamic properties. Furthermore, in some embodiments, stabilization arches may be provided that are connected to the valve fixation arches in order to increase the free area between the three valve fixation arches and thus improve the blood flow to the coronary arteries. The specific design of the stabilization arches with a gradual stiffness change allows the stabilization arches to work independently of the valve fixation arches (see e.g., FIG. 11). The three stabilization arches may reinforce in this configuration the three valve fixation arches and thus reduce their deflection towards the longitudinal axis of the stent under diastolic pressure. Thus, according to some embodiments of the present disclosure, the stabilization arches may be designed to be independent of the valve fixation devices. See FIG. 11A. According to some embodiments of the present disclosure, the stabilization arches may be designed with gradual stiffness change and connected to valve fixation arches. See FIG. 11B.

These four stent sections may be formed, for example, by laser cutting a tube or single sheet of material (e.g., nitinol). For example, the stent may be cut from a tube and then step-by-step expanded up to its final diameter by heat treatment on a mandrel. As another example, the stent may be cut from a single sheet of material, and then subsequently rolled and welded to the desired diameter.

FIG. 1A is a side view of a stent component 100 for supporting a replacement valve, according to some embodiments of the present disclosure, which is generally symmetrical in the vertical plane about a longitudinal axis 101. The stent component may be self-expanding and/or may be expanded via, for example, a balloon. Such stents may be formed from a suitable material familiar to those of skill in the art, which may include, for example, stainless steel or a shape-memory material (e.g., nitinol) or a combination of materials. In some embodiments, the stent component may be laser cut from a single tube or sheet of such material(s).

As shown in FIG. 1A, the stent component may comprise a plurality of sections. For example, such a stent may comprise four sections: 102, 104, 106, 108). Stent section 102, for example, may define a proximal end of the stent component. In some embodiments of the present disclosure, stent section 102 may be generally conically shaped, and represent a section of a cone (e.g., a truncated cone, frustrum, etc.), having a first plane of a first smaller diameter, and a second plane spaced apart from the first plane and having a second larger diameter than the first diameter. In some embodiments, the two planes may be parallel.

According to some embodiments, stent section 102 has a shape and size configured such that it may create a form fit with one side (e.g., the inflow side) of the cardiac valve being replaced (e.g., aortic valve), for example, and therefore prevent migration of the valved-stent. If the stent is used in an aortic valve replacement, the fit of section 102 that prevents {or substantially prevents) migration of the valved-stent towards the ascending aorta (or prevents migration of the stent component if the stent is used as a positioning stent for receiving a second stent having the valve component). Furthermore,section 102 may provide a radial force, for example, that creates an additional friction fit against the inflow tract/aortic annulus.

The second stent section 104 also may also have a generally conical shape, according to some embodiments, and like section 102, may represent a section of a cone (e.g., a truncated cone, a frustrum, etc.) having a first plane of a first smaller diameter, and a second plane spaced apart from the first plane and having a second larger diameter than the first diameter. In some embodiments, the two planes may be parallel. Blood flow may be in the direction shown in FIG. 1A by arrow 110.

In some embodiments, the first planes of section 102 and section 104, having the smaller radii, match (or substantially match) and lie immediately adjacent one another, and may be joined thereto as well. Thus, such an arrangement may correspond to two inverted frustums. According to some embodiments, stent section 104 has a size and shape configured such that it may create a form fit with a second tract of the valve being replaced (e.g., the outflow tract/native leaflets of the aortic valve). If the stent is used for an aortic valve replacement, the fit of section 104 may prevent (or substantially prevent) migration of the valved-stent towards the left ventricle (or may prevent/substantially prevent migration of the stent component if the stent is used as a positioning stent for receiving a second stent having the valve component). Furthermore, stent section 104 may also provide a radial force that creates an additional friction fit against the valve annulus (e.g., aortic annulus/outflow tract/ native leaflets, for example (e.g., an aortic valve replacement).

The third stent section 106, which may overlap with stent section 104, and may also have a generally conical shape, according to some embodiments, but in other embodiments, a substantial portion or all of section 106 preferably more cylindrical in shape. Section 106 preferably designates the portion of the stent component to which the valve component/prosthesis may be affixed onto the stent component. According to some embodiments, stent section 106 may comprise a plurality of (e.g., two, three, four, five, six, eight, etc.) arches which may be used, for example, for the fixation of the valve commissures. In some embodiments, one or more of the arches may also comprise additional reinforcements for fixation of the valve prosthesis.

The fourth stent section 108, according to some embodiments, may define a distal end of the stent component. In some embodiments, stent section 108 may have a generally conical shape, with the slant height of the conical shape oriented at an angle having a direction which may correspond to a direction of the angle of the slant height of stent section 104. In some embodiments, stent section 108 may comprise a plurality of (e.g., two, three, four, five, six, eight, etc.) arches, which may be larger than the arches noted for section 106, where such arches may also be aligned in the same direction with the arches of stent section 106. These larger arches may be the first components of the stent to be deployed during the distal to proximal release of the valved-stent from its first, unexpanded configuration to its second, expanded configuration in a cardiac valve replacement, for example, an aortic valve replacement. In such an aortic valve replacement, the deployed section 108 arches may be used to engage the ascending aorta thereby orientating the delivery system/valved-sent longitudinally within the aorta/aortic annulus, thus preventing any tilting of the implanted valved-stent. In some embodiments, a radiopaque marker 112 may be positioned on or close to an end (e g., the distal end) of at least one of the arches. A function of such a radiopaque marker is described below in connection with FIGS. 15A-D.

In some embodiments, the larger arches of stent section 108 may be at least partially of cylindrical shape when fully expanded and may deform to a conical shape when only partially deployed. This may result in lower local stresses in the aortic wall, thus reducing the risks of inflammation/perforation.

In some embodiments, the overall stent length may be sufficiently small so as to avoid conflict with, for example, the mitral valve when the stent is being used for aortic valve replacement. Of course, it will be understood that these dimensions will vary depending on, for example, the type of valve used and the dimensions given above are included as examples only and other sizes/ranges arc available which conform to the present disclosure.

In still other embodiments of the present disclosure, a replacement valve for use within a human body is provided that includes a valve component, a stent component for housing the valve component, and at least two skirts (e.g., polyester (PET) skirts). An inner skirt may be provided that covers at least a portion (e.g., all) of an outer surface of the valve component, where the inner skirt may be sutured to at least the inflow tract of the valve component and to an inner surface of the stent. An outer skirt may also be provided that is sutured onto an outer surface of the stent.

Figure 1B:
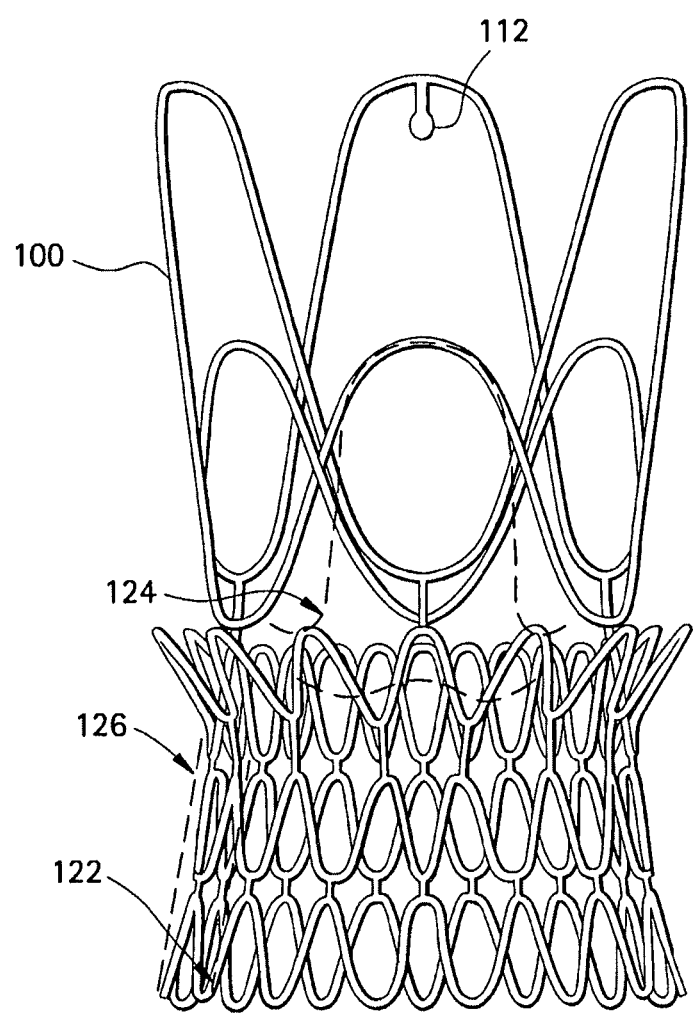
FIG. 1B shows the placement of a double polyester (PET) fabric skirt (dashed line representing inner PET fabric skirt 122 and outer PET fabric skirt 126) relative to a stent component, as well as placement of a valve-component within the stent (e.g., aortic biologic valve prosthesis, dashed line 124).

FIG. 1B shows one embodiment of a self-expanding stent 100. FIG. 1B shows the placement of a double polyester (PET) fabric skirt (dashed line representing inner PET fabric skirt 122 and outer PET fabric skirt 126) relative to a stent component, as well as placement of a valve-component within the stent (eg., aortic biologic valve prosthesis, dashed line 124), according to some embodiments of the present disclosure. An inner skirt may cover at least a portion—for example, either a minor portion (e.g., less than about 20% coverage), a substantial portion (e.g., about 50-90% coverage), or all (e.g., 90%+) of the stent) of the outer surface of the replacement valve. The skirt may be sutured to at least the inflow tract of the valve and to the inner surface of the stent, and may serve as a sealing member between the stent and the valve. In some embodiments, the topology of the inner surface of this fabric may be configured to improve blood flow. An outer skirt may also be sutured onto the outer surface of the stent (dashed line 126) and may serve as a sealing member between the stent and, for example, a native valve leaflets/cardiac valve (e.g., aortic) annulus/inflow and/or outflow tract. In some embodiments, the topology of the outer surface of this fabric may be configured to improve endothelialisation, for example. The skirt may be made using any know material used for such purposes. Preferably, the skirt is comprised of a polyester material, such as a single ply polyester material. The preferred polyester is polyethylene terephthalate (PET).

Figure 12:
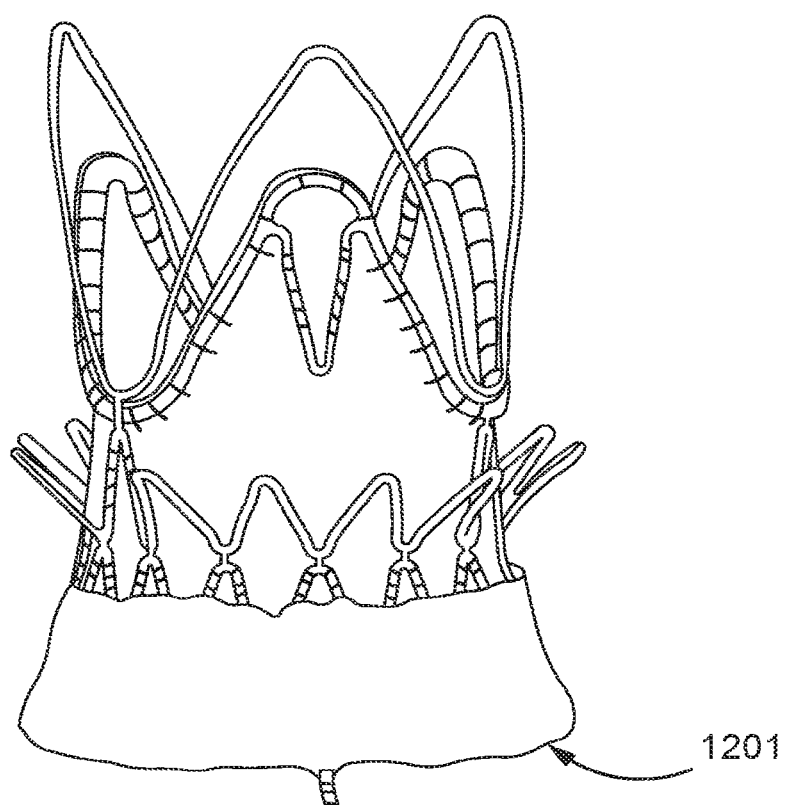
FIG. 12 illustrates a placement of a double polyester (PET) fabric skirt relative to a stent component, according to some embodiments of the present disclosure.

A double PET fabric skirt may be provided in which the free edge of the stent is covered to avoid injuries of the left ventricle wall and mitral valve (see e.g., FIG. 12).

Figure 2A:
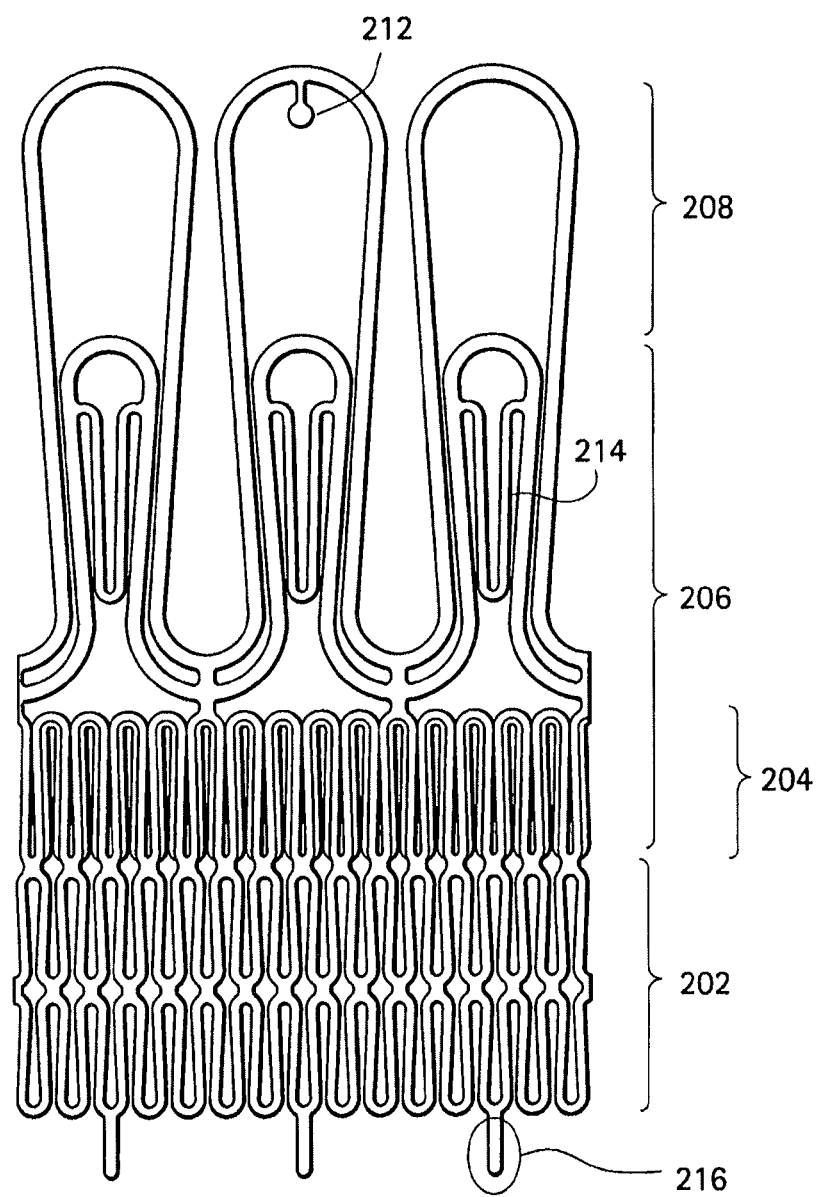
FIG. 2A shows an unrolled, flat depiction of another embodiment of a stent component according to some embodiments of the present disclosure.

FIG. 2A shows an unrolled, flat depiction of another embodiment of a stent component according to some embodiments of the present disclosure. This stent component may be the same or similar to the stent component of FIG. 1, and include the same numbering scheme as set out for FIG. 1, except that the corresponding reference numeral starts with a "2" instead of a "1". The stent component illustrated in FIG. 2A includes some additional features, mainly one or more additional reinforcements 214 for stent section 206, as well as one or more attachment elements 216 in stent section 202. This numbering scheme is generally used throughout the specification.

Figure 18A:
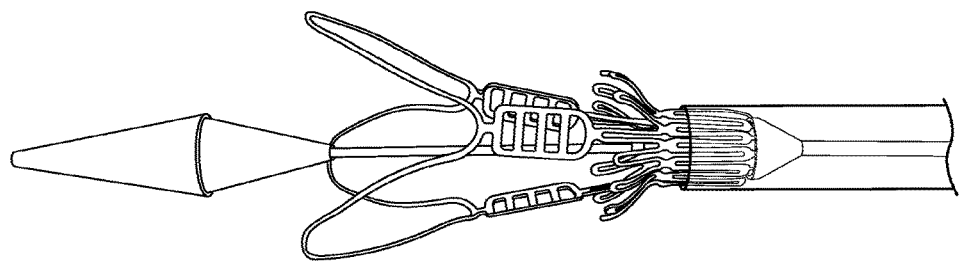
FIGS. 18A-C illustrate the full release of a stent according to some embodiments of the present disclosure.
Figure 18B:
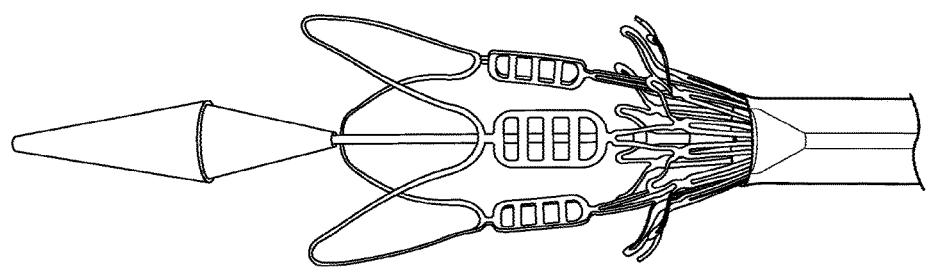
Figure 18C:
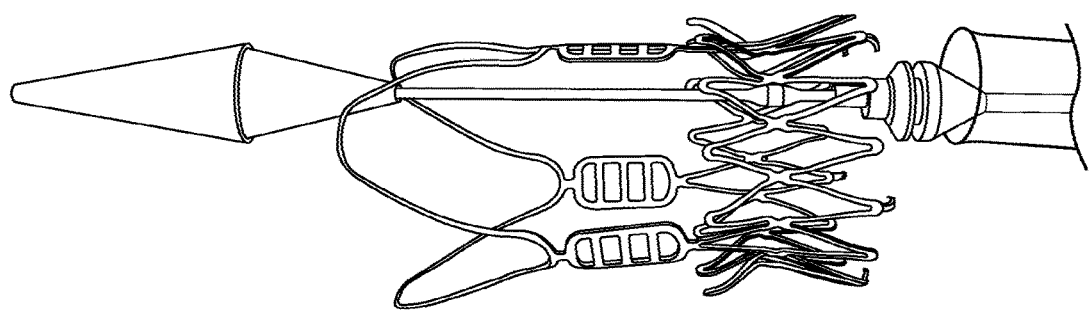

Additional reinforcements 214 may comprise arches, which may be inverted as compared to the commissural arches currently provided in stent section 206. Attachment elements 216 may be used to removable attach the stent component to a delivery device (e.g., a catheter based system). In some embodiments, elements 216 may serve to hold the stent-valve onto the delivery system until full release of the stent during delivery/implantation, thus allowing for, in some embodiments, the recapture of the stent upon partial release. See FIG. 16-18. The attachment elements 216 may also prevent the stent from 'jumping out" of the delivery system just prior to its full release—such jumping out may result in inaccurate positioning of the replacement valve.

In some embodiments, a radiopaque marker 212 may be positioned on or close to an end (e.g., the distal end) of at least one of the arches. A function of such a radiopaque marker is described below in connection with FIGS. 15A-D.

Figure 2B:
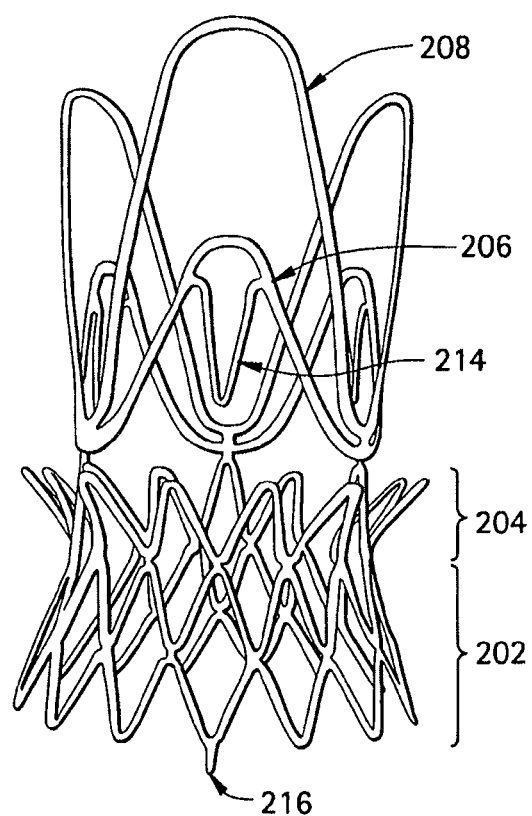
FIG. 2B is a side view of a stent component shown in FIG. 2A.

FIG. 2B show another design of the devices of the current embodiments. The stent component illustrated in FIG. 2A-B includes some additional features, mainly one or more additional reinforcements 214 for stent section 206, as well as one or more attachment elements 216 in stent section 202. Such attachment elements may be formed generally in the shape of a bent, or curved angled member (e.g., an "L" or "J" like shape). In some embodiments, such attachment elements may be a hook (e.g., a "J" like shape).

Some embodiments of the present disclosure include, for example stents and valved-stents: for anchoring towards the ascending aorta; for anchoring towards the left ventricle; for valve fixation; and/or for valved-stent stabilization, as well as other possible applications.

Figure 3A:
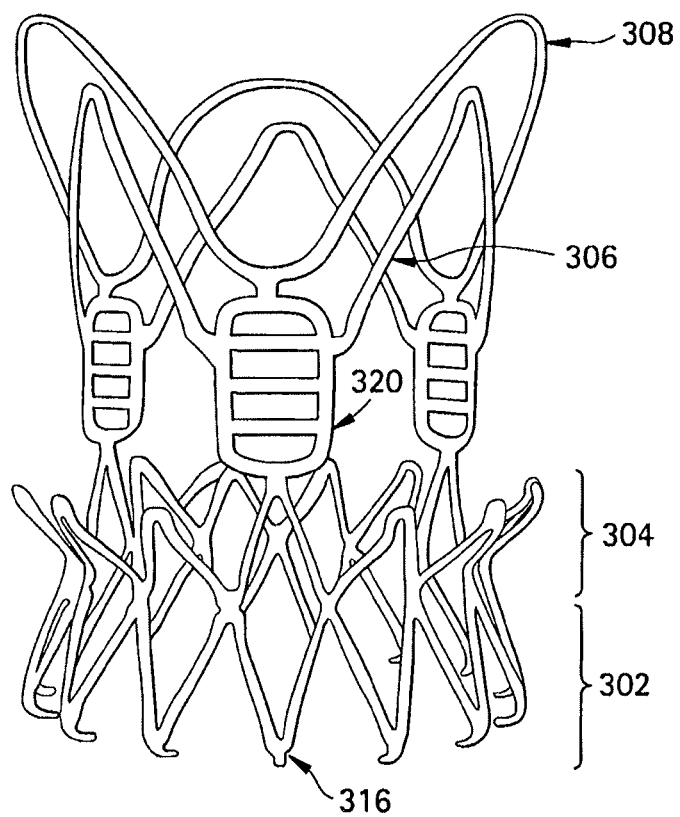
FIG. 3A show a stent design with longitudinal elements for commissural valve fixation.
Figure 3B:
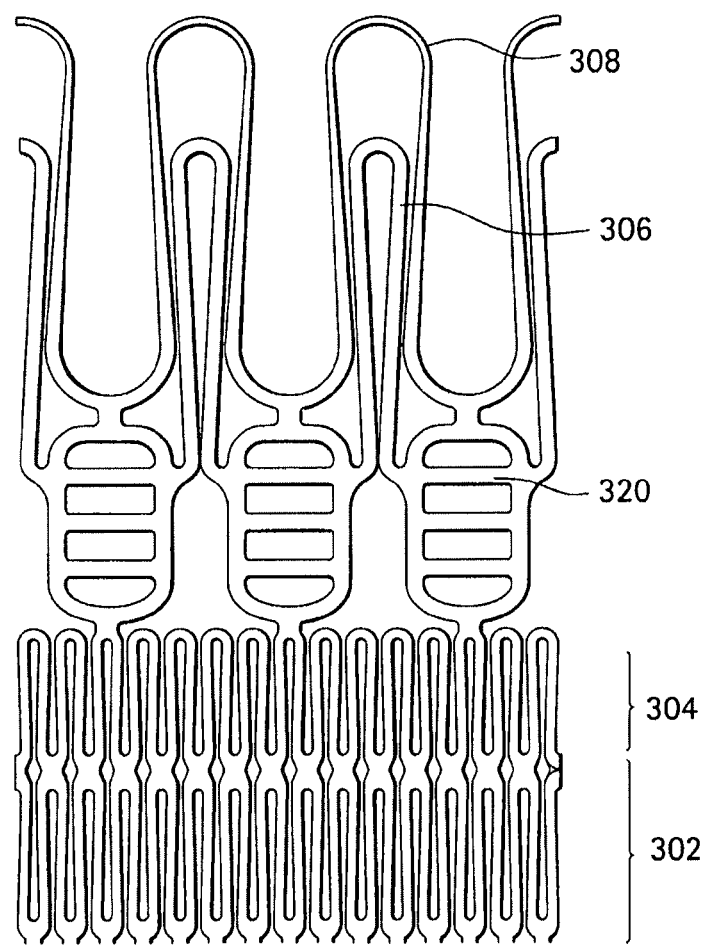
FIG. 3B shows an unrolled, flat depiction of the stent design of FIG. 3A.
Figure 4:
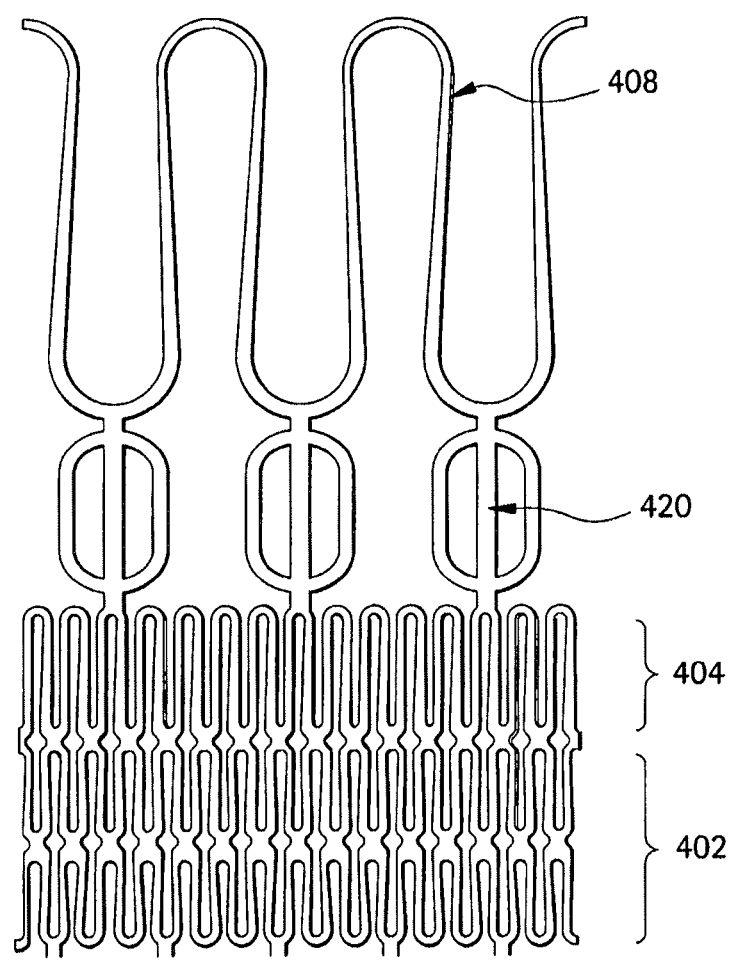
FIG. 4 shows an unrolled, flat depiction of an alternative design based on similar embodiments, without reinforcement crown.

FIGS. 3A-B and 4 show examples of stent designs based on such embodiments.

FIGS. 3A and 3B show a stent design with longitudinal elements for commissural valve fixation. FIG. 3B shows an unrolled, flat depiction of the above stent design. These figures show the stabilization arch 308 (conically shaped section), reinforcement crown 306 (cylindrical section), longitudinal valve fixation elements 320 (cylindrical section), forward anchoring crown 304 (e.g., towards LV or otherwise preventing movement of device in a direction opposite of blood flow) (conically shaped section), and reverse anchoring crown 302 (e.g., towards ascending aorta or otherwise preventing movement of device in the direction of blood flow) (conically shaped section).

An unrolled, flat depiction of an alternative design for a stent without reinforcement crowns is in FIG. 4. FIG. 4 shows the stabilization arch 408 (conically shaped section), longitudinal valve fixation elements 420 (cylindrical section), forward anchoring crown 404 (e.g., towards LV or otherwise preventing movement of device in the direction of blood flow) (conically shaped section), and reverse anchoring crown 402 (e.g., towards ascending aorta or otherwise preventing movement of device in a direction opposite of blood flow) (conically shaped section). The reverse anchoring crown 402 may be comprised of two rows (plurality) of meanders for improved stability. In preferred embodiments, the fixation elements 420 together help to form the cylindrical shape of the optional third section of the stent. That is, the fixation elements 420 are preferably curved around the longitudinal axis of the stent and, in some embodiments, may form the circumference of the third section of the stent.

In some embodiments, a stent is presented which includes a section for commissural valve fixation which is composed of a plurality (e.g., two, three, four, five, six, eight, etc.) longitudinal elements connected on one side to a conically shaped section (for example) used for anchoring towards the left ventricle and on the other side to the conically shaped section (for example) used for stabilization.

According to some embodiments, the stent is designed to better match the size and shape of a biological valve with narrow commissural posts and, in some embodiments, allow a more robust suturing of the valve commissural posts to the stent. Narrow commissural posts according to some embodiments improve the perfusion of the coronary arteries via the sinus of vasalva. To reduce the deflection of the three longitudinal elements under diastolic pressure, an additional reinforcement crown may be added as well in some embodiments.

According to some embodiments, the stent design allowing for the fixation of the valve commissural posts, according to some embodiments, provides a further advantage, as the size and shape of such stents preferably does not change substantially, and even more preferably, does not change during a required crimping process for loading the stent (with valve, "valved-stent") onto a delivery catheter. Accordingly, this may reduce (and preferably does reduce) the risks of suture damage and facilitating crimping and subsequently releasing of the valved-stent (for example).

Although a number of embodiments are herein described, other modifications are possible, and thus, the noted embodiments are for illustrative purposes only.

Figure 5:
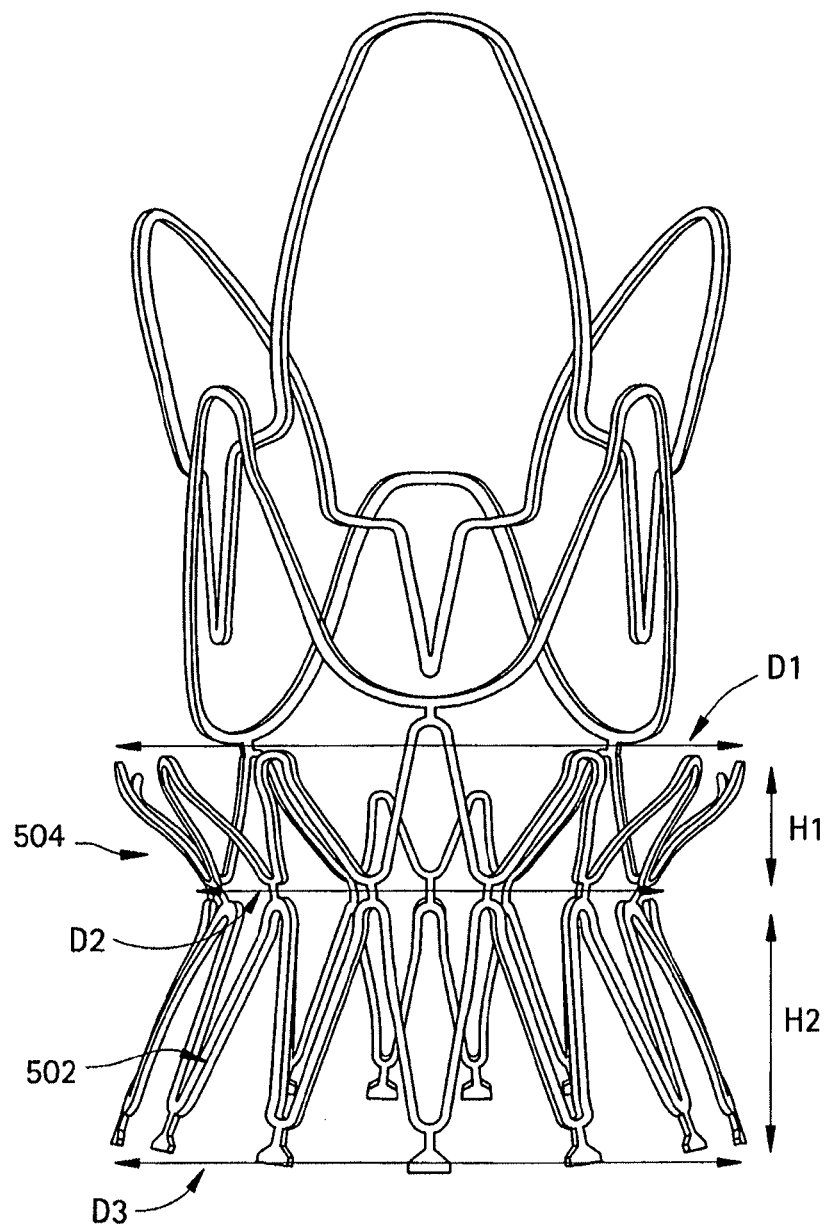
FIG. 5 and FIG. 6 show the size and shape of the anchoring crowns for the stent component in the expanded configuration according to some embodiments of the disclosure.

FIG. 5 is provided to illustrate the dimensions of the first and second sections of the stent component. With respect to the first section, D3 represents the diameter of the most proximal edge of the stent component in the expanded configuration. D2 represents the diameter of the stent component at the juncture between the first conical section 502 and second conical section 504 of the stent component. H2 represents the axial distance between the planes of the diameters D2 and D3 in the expanded configuration, or the length of the first conical section in the expanded configuration. D1 represents the diameter of the most distal edge of the second conical section of the stent component in the expanded configuration. H1 represents the axial distance between the planes of the diameters D1 and D2 in the expanded configuration, or the length of the second conical section in the expanded configuration.

Preferably, the length of the first conical section H2 is between about 3 to about 15 mm (e.g., about 3 mm, about 4 mm, about 5 mm, about 6 mm, about 7 mm, about 8 mm, about 9 mm, about 10 mm, about 11 mm about 12 mm, about 13 mm, about 14 mm, and about 15 mm). The length of the first conical section H2 may been adjusted depending on the intended application of the stent of stent-valve. For example, the length of the first conical section H2 may range from about 3 to about 5 mm, about 3 to about 7 mm, about 3 to about 12 mm, about 3 to about 15 mm, about 3 to about 20 mm, about 5 to about 10 mm, about 5 to about 12 mm, about 5 to about 15 mm, about 7 to about 10 mm, about 7 to about 12 mm, about 7 to about 15 mm, about 10 to about 13 mm, about 10 to about 15 mm, or about 7 to about 20 mm. For example, the length of this section may be on the smaller end of the scale to avoid potential conflict with a cardiac valve, such as the mitral valve.

The diameter of the first conical section at D3 is preferably between about 22 mm to about 40 mm (e.g., about 22 111111, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, and about 40 mm). This diameter of the first conical section D3 may been adjusted depending on the intended application of the stent of stent-valve. Thus, the diameter of the first conical section in the expanded configuration D3 may be from between about 15 mm to about 50 mm, from between about 15 mm to about 40 mm, from between about 20 mm to about 40 mm, from between about 24 mm to about 40 mm, from between about 26 mm to about 40 mm, from between about 28 mm to about 40 mm, from between about 30 mm to about 40 mm, from between about 32 mm to about 40 mm, from between about 34 mm to about 40 mm, from between about 36 mm to about 40 mm, from between about 38 mm to about 40 mm, from between about 22 mm to about 38 mm, from between about 22 mm to about 36 mm, from between about 22 mm to about 34 mm, from between about 22 mm to about 32 mm, from between about 22 mm to about 30 mm, from between about 22 mm to about 28 mm, from between about 24 mm to about 34 mm, from between about 25 mm to about 35 mm, or from between about 25 mm to about 30 mm.

The diameter of the stent component D2 at the juncture of the first and second conical sections D2 is preferably between about 20 mm to about 30 mm (e.g., about 20 mm, about 21 mm, about 22 mm, about 23 mm, about 24 mm, about 25 mm, about 26 mm, about 27 mm, about 28 mm, about 29 mm, and about 30 mm). This diameter of the stent component D2 may been adjusted depending on the intended application of the stent of stent-valve. For example, this diameter of the stent component D2 may be sized according to the shape of the annulus of the cardiac valve. Thus, the diameter of the stent component D2 may be from between about 15 mm to about 40 mm, from between about 15 mm to about 30 mm, from between about 18 mm to about 35 mm, from between about 22 mm to about 30 mm, from between about 24 mm to about 30 mm, from between about 26 mm to about 30 mm, from between about 28 mm to about 30 mm, from between about 22 mm to about 28 mm, from between about 22 mm to about 26 mm, from between about 20 mm to about 24 mm, from between about 20 mm to about 26 mm, from between about 20 mm to about 28 mm, and from between about 22 mm to about 32 1 mn.

The diameter of the second conical section at D1 is preferably between about 22 mm to about 40 mm (e.g., about 22 mm, about 23 mm, about 24 mm, about 25 lmn, about 26 mm, about 27 mm, about 28 mm, about 29 mm, about 30 mm, about 31 mm, about 32 mm, about 33 mm, 34 mm, 35 mm, 36 mm, 37 mm, about 38 mm, about 39 mm, and about 40 mm). This diameter of the second conical section D1 may been adjusted depending on the intended application of the stent of stent-valve. Thus, the diameter of the first conical section in the expanded configuration D1 may be from between about 15 mm to about 50 mm, from between about 15 mm to about 40 mm, from between about 20 mm to about 40 mm, from between about 24 mm to about 40 mm, from between about 26 mm to about 40 mm, from between about 28 mm to about 40 mm, from between about 30 mm to about 40 mm, from between about 32 mm to about 40 mm, from between about 34 mm to about 40 mm, from between about 36 mm to about 40 mm, from between about 38 mm to about 40 mm, from between about 22 mm to about 38 mm, from between about 22 mm to about 36 mm, from between about 22 mm to about 34 mm, from between about 22 mm to about 32 mm, from between about 22 mm to about 30 mm, from between about 22 mm to about 28 mm, from between about 24 mm to about 34 mm, from between about 25 mm to about 35 mm, or from between about 25 mm to about 30 mm.

Preferably, the length of the second conical section H1 is between about 3 to about 10 mm (e.g., about 3 mm, about 4 mm, about 5 mm, about 6 mm, about 7 mm, about 8 mm, about 9 mm, and about 10 mm). The length of the first conical section H1 may been adjusted depending on the intended application of the stent of stent-valve. For example, the length of the first conical section H2 may range from about 3 to about 5 mm, about 3 to about 15 mm, about 3 to about 20 mm, about 5 to about 10 mm, about 7 to about 10 mm, about 7 to about 12 mm, about 7 to about 15 mm, about 10 to about 13 mm, about 5 to about 15 mm, about 7 to about 20 mm. For example, the length of this section may be on the smaller end of the scale to avoid potential conflict with a cardiac valve, such as the mitral valve.

Figure 6:
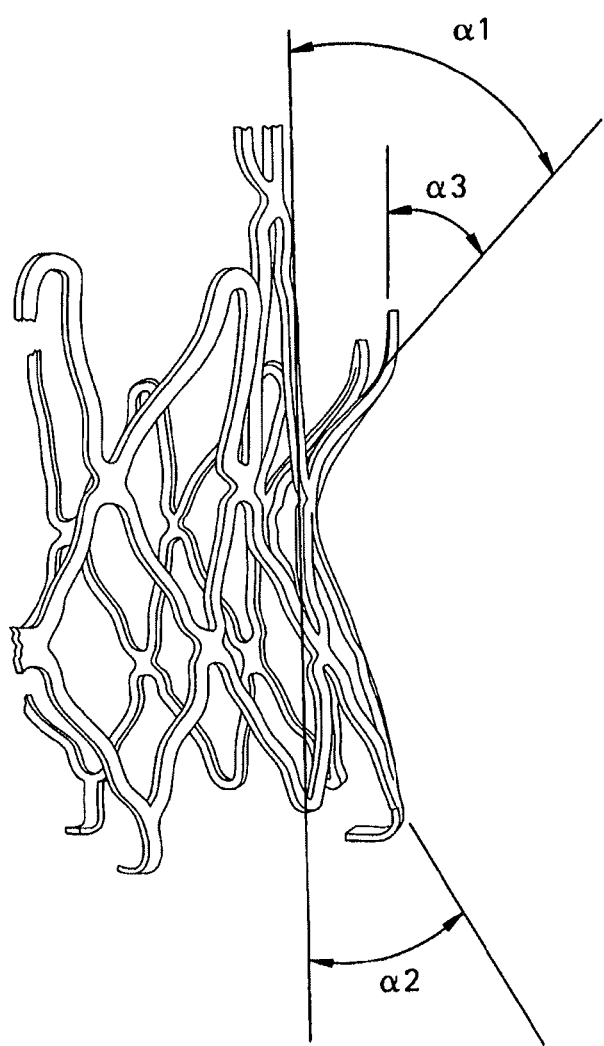

FIG. 6 is provided to illustrate the dimensions of the first and second sections of the stent component, and particularly the angles of the anchoring crowns that help to define these conical sections. The u1 angle defines the angle of the anchoring crown of the second conical section of the stent component in the expanded configuration. The u2 angle defines the angle of the anchoring crown of the first conical section of the stent component in the expanded configuration. The u3 angle defines the angle of bending of the tip, which is done so as to prevent injuries of sinus (see also, FIG. 10).

The a1 angle is preferably between from about 10 degree to about 80 degree (e.g., about 10 degree, about 15 degree, about 20 degree, about 25 degree, about 30 degree, about 35 degree, about 40 degree, about 45 degree, about 50 degree, about 55 degree, about 60 degree, about 65 degree, about 70 degree, about 75 degree, and about 80 degree), more preferably between from about 20 degree to about 70 degree, most preferable between from about 30 degree to about 60 degree. According to some embodiments, the a1 angle is between from about 20 degree to about 80 degree, between from about 20 degree to about 60 degree, between from about 20 degree to about 50 degree, between from about 20 degree to about 45 degree, between from about 40 degree to about 60 degree, between from about 45 degree to about 60 degree, between from about 30 degree to about 50 degree, between from about 30 degree to about 45 degree, between from about 30 degree to about 40 degree, or between from about 25 degree to about 45 degree.

The a2 angle is preferably between from about 5 degree to about 50 degree (e.g., about 5 degree, about 10 degree, about 15 degree, about 20 degree, about 25 degree, about 30 degree, about 35 degree, about 40 degree, about 45 degree, and about 50 degree), more preferably between from about 10 degree to about 40 degree, most preferable between from about 10 degree to about 30 degree. According to some embodiments, the a2 angle is between from about 5 degree to about 45 degree, between from about 5 degree to about 40 degree, between from about 5 degree to about 30 degree, between from about 5 degree to about 25 degree, between from about 5 degree to about 20 degree, between from about 5 degree to about 15 degree, between from about 10 degree to about 20 degree, between from about 10 degree to about 25 degree, between from about 10 degree to about 30 degree, between from about 10 degree to about 40 degree, between from about 10 degree to about 45 degree, between from about 15 degree to about 40 degree, between from about 15 degree to about 30 degree, between from about 15 degree to about 25 degree, between from about 20 degree to about 45 degree, between from about 20 degree to about 40 degree, or between from about 20 degree to about 30 degree The a3 angle is preferably between from about 0 degree to about 180 degree (e.g., about 5 degree, about 10 degree, about 15 degree, about 20 degree, about 25 degree, about 30 degree, about 35 degree, about 40 degree, about 45 degree, about 50 degree, about 55 degree, about 60 degree, about 65 degree, about 70 degree, about 75 degree, about 80 degree, about 85 degree, about 90 degree, about 95 degree, about 100 degree, about 105 degree, about 110 degree, about 115 degree, about 120 degree, about 125 degree, about 130 degree, about 135 degree, about 140 degree, about 145 degree, about 150 degree, about 155 degree, about 160 degree, about 165 degree, about 170 degree, about 175 degree, and about 180 degree). According to some embodiments, the a3 angle is between from about 45 degree to about 90 degree, between from about 45 degree to about 180 degree, between from about 60 degree to about 90 degree, between from about 45 degree to about 120 degree, between from about 60 degree to about 120 degree, between from about 90 degree to about 120 degree, between from about 90 degree to about 180 degree, or between from about 120 degree to about 180 degree.

Figure 7:
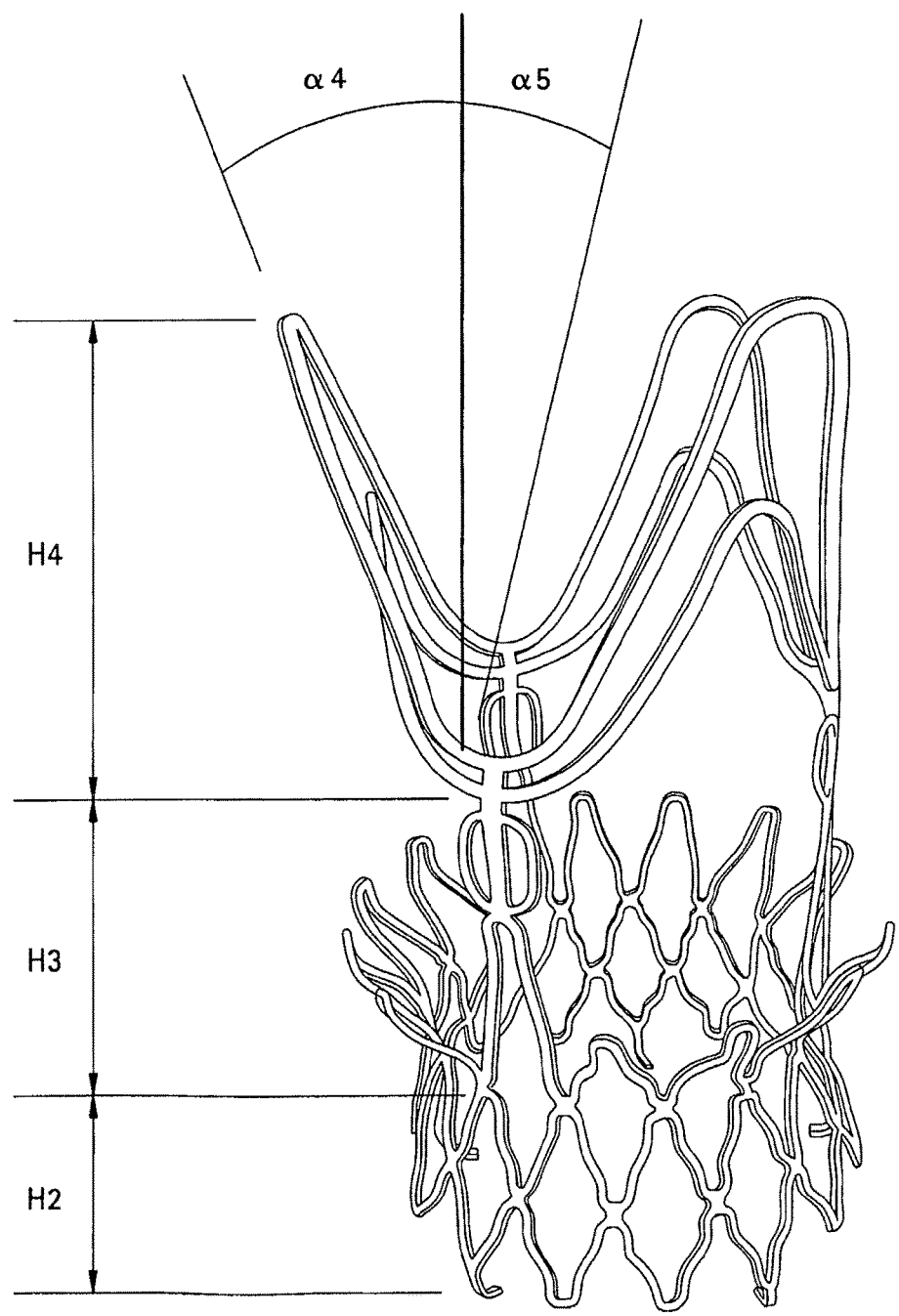
FIG. 7 shows the size and shape of stabilization arches for the stent component in the expanded configuration according to some embodiments of the disclosure.

FIG. 7 shows the size and shape of stabilization arches for the stent component in the expanded configuration according to some embodiments of the disclosure. The a4 and a5 angles represent the offset angle from a longitudinal axis of the stabilization arches of the forth section of the stent in the expanded configuration. If the stabilization arches are directed away from the center of the stent, the a4 angle is used. If the stabilization arches are directed toward from the center of the stent, the a5 angle is used.

The a4 angle is preferably between from about 0 degree to about 60 degree (e.g., about 5 degree, about 10 degree, about 15 degree, about 20 degree, about 25 degree, about 30 degree, about 35 degree, about 40 degree, about 45 degree, about 50 degree, about 55 degree, and about 60 degree). According to some embodiments, the a4 angle is between from about 20 degree to about 60 degree, between from about 30 degree to about 60 degree, between from about 40 degree to about 60 degree, between from about 45 degree to about 60 degree, between from about 30 degree to about 50 degree, between from about 30 degree to about 45 degree, between from about 20 degree to about 40 degree, or between from about 15 degree to about 45 degree.

The a5 angle is preferably between from about 0 degree to about 20 degree (e.g., about 5 degree, about 10 degree, about 15 degree, and about 20 degree). According to some embodiments, the a5 angle is between from about 5 degree to about 20 degree, between from about 10 degree to about 20 degree, between from about 15 degree to about 20 degree, between from about 0 degree to about 15 degree, between from about 0 degree to about 10 degree, between from about 5 degree to about 15 degree, between from about 10 degree to about 15 degree, or between from about 10 degree to about 20 degree.

FIG. 7 also shows the length of the first section of the stent component H2, the length of the combined second section and optional third section of the stent component H3, and the length of the forth section of the stent component H1. H2 is as described above.

Preferably, the length of the combined second section and optional third section of the stent component H3 is between about 3 to about 50 mm (eg., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 20 mm, about 22 mm, about 24 mm, about 25 mm, about 26 mm, about 28 mm, about 30 mm, about 32 mm, about 34 mm, about 36 mm, about 38 mm, about 40 mm, about 42 mm, about 44 mm, about 45 mm, about 46 mm, about 48 mm, and about 50 mm). The length of the first conical section H3 may been adjusted depending on the intended application of the stent of stent-valve. For example, the length of the first conical section H3 may range from about 3 to about 40 mm, about 3 to about 30 mm, about 3 to about 20 mm, about 3 to about 10 mm, about 10 to about 50 mm, about 10 to about 40 mm, about 10 to about 30 mm, about 10 to about 20 mm, about 15 to about 50 mm, about 15 to about 40 mm, about 15 to about 30 mm, about 20 to about 50 mm, about 20 to about 40 mm, about 20 to about 30 mm, about 15 to about 50 mm, about 25 to about 50 mm, about 30 to about 50 mm, about 40 to about 50 mm, about 15 to about 40 mm, about 25 to about 40 mm, or about 30 to about 40 mm. According to some embodiments of the stent component, the third section of the stent component is not used. Thus, H3 would be the same as HI, described above.

Preferably, the length of the forth section and of the stent component H4 is between about 5 to about 50 mm (e.g., about 5 mm, about 6 mm, about 7 mm, about 8 mm, about 9 mm, about 10 mm, about 11 mm, about 12 mm, about 13 mm, about 14 mm, about 15 mm, about 20 mm, about 22 mm, about 24 mm, about 25 mm, about 26 mm, about 28 mm, about 30 mm, about 32 mm, about 34 mm, about 36 mm, about 38 mm, about 40 mm, about 42 mm, about 44 mm, about 45 mm, about 46 mm, about 48 mm, and about 50 mm). The length of the first conical section H4 may have been adjusted depending on the intended application of the stent of stent-valve. For example, the length of the first conical section H4 may range from about 5 to about 40 mm, about 5 to about 30 mm, about 5 to about 20 mm, about 5 to about 10 mm, about 10 to about 50 mm, about 10 to about 40mm, about 10 to about 30 mm, about 10 to about 20 mm, about 15 to about 50 mm, about 15 to about 40 mm, about 15 to about 30 mm, about 20 to about 50 mm, about 20 to about 40 mm, about 20 to about 30 mm, about 15 to about 50 mm, about 25 to about 50 mm, about 30 to about 50 mm, about 40 to about 50 mm, about 15 to about 40 mm, about 25 to about 40 mm, or about 30 to about 40 mm.

Using the dimensions described above (i.e., D1, D2, D3, H1, H2, H3, H4, u1, u2, u3, and u4), the stent components of the stent-valves according to some embodiments of the present disclosure may be classified into different categories of sizes, such as small, medium, and large. Thus, according to some embodiments, the stent components (or stent valves) may be sized as small, medium, and large according the following table.

| Small | | Medium | Large |
|---|---|---|---|
| D1 [mm] | 26-31 | 27-32 | 28-33 |
| D2 [mm] | 20-25 | 21-26 | 22-27 |
| D3 [mm] | 26-32 | 27-33 | 28-34 |
| HI [mm] | 4-8 | 4-8 | 4-8 |
| H2 [mm] | 7-11 | 8-12 | 9-13 |
| H3 [mm] | 11-15 | 13-17 | 15-19 |
| H4 [mm] | 14-22 | 15-23 | 16-24 |
| u 1 | 45°-65° | 45°-65° | 45°-65° |
| u2 | 15°-25° | 15°-25° | 15°-25° |
| u3 | 45°-65° | 45°-65° | 45°-65° |
| u4 | 5°-15° | 5°-15° | 5°-15° |

Figure 8:
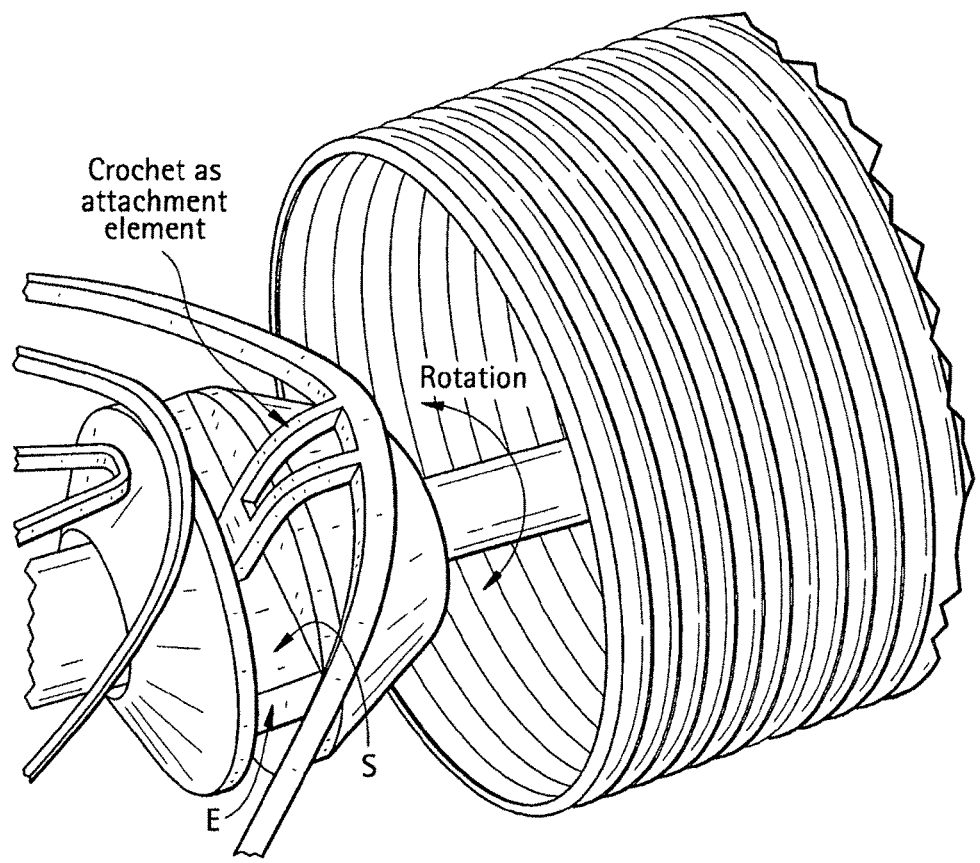
FIG. 8 shows a mating couple between attachment elements of the stent component and a stent-holder of a delivery device, according to some embodiments of the present disclosure.

FIG. 8 shows a mating coupling between the attachment elements 316 of the stent and a stent-holder of a delivery device, according to some embodiments of the present disclosure. As shown, at least one, and preferably a plurality or all of the attachment elements may include a crochet-like configuration that engages, for example, a groove or other opening within the stent holder. Such attachment elements may be formed generally in the shape of a bent, or curved angled member (e.g., an "L" or "J" like shape). In some embodiments, such attachment elements may be a hook (e.g., a "J" like shape). In the embodiment illustrated in FIG. 8, the attachment element may be provided in an angled shape, for example, that extends from the body of the stent inwardly toward a central, longitudinal axis of the stent. The opening in the stent holder (e.g., groove) may allow for a safe release of the stent upon rotation of the delivery system (e.g., a portion, all or members thereof—e.g., rotation of the stent holder). For example, when rotating the delivery system/stent holder, the end of the attachment element slides onto the surface "S" and is thereby forced, according to some embodiments, to disengage the stent holder when reaching the edge "E".

Figure 9:
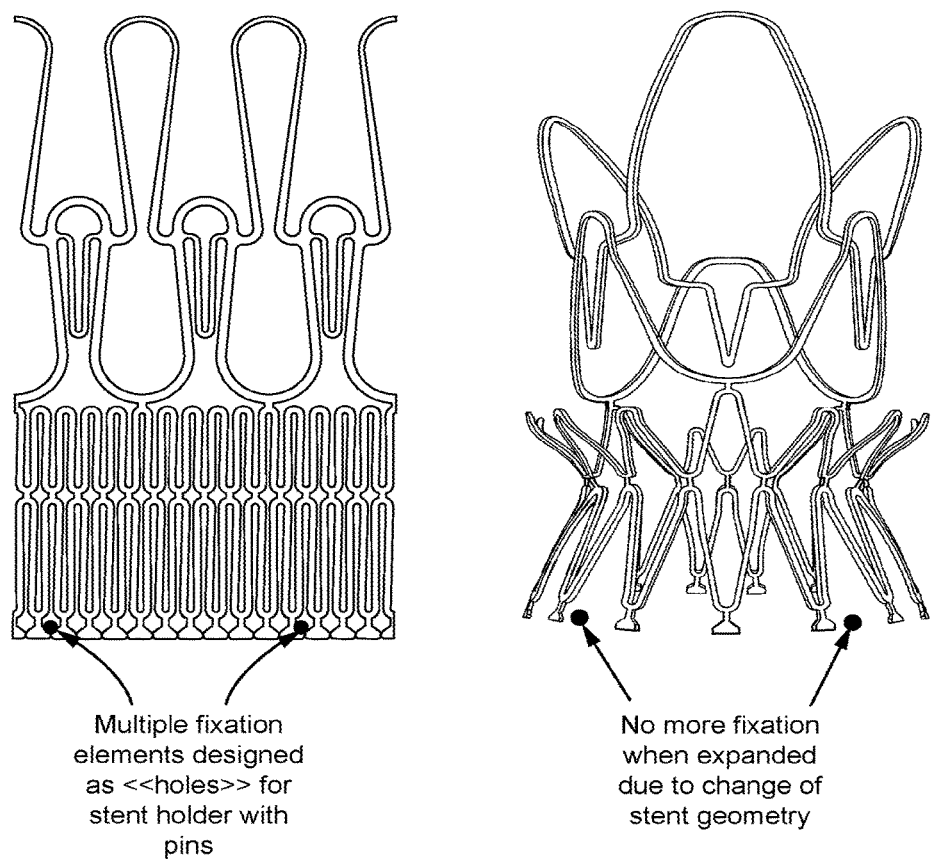
FIG. 9 shows the design of multiple fixation elements (e.g., "holes") that allow for the fixation of the stent onto the catheter when the stent is crimped or in the collapsed configuration.
Figure 13:
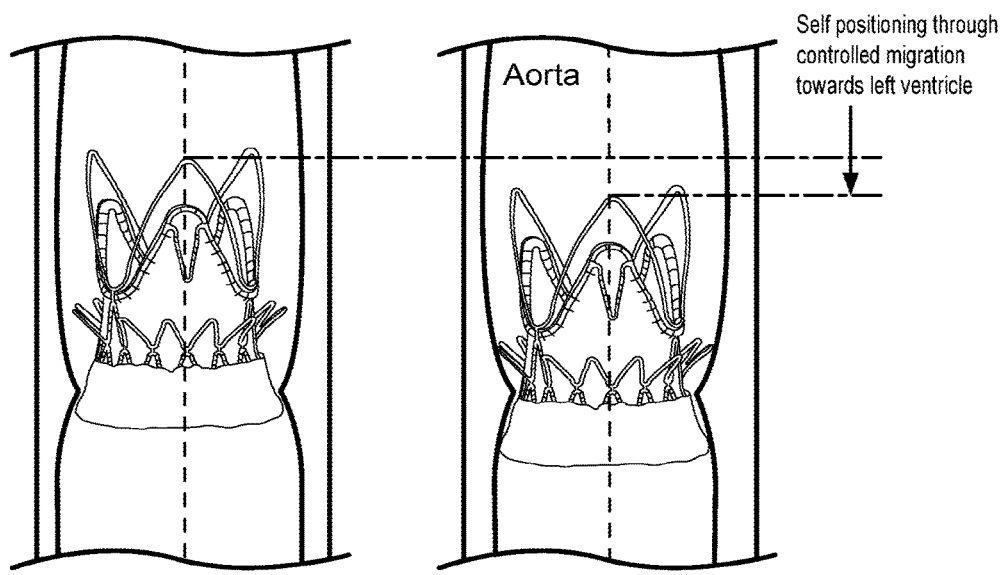
FIG. 13 shows the in vivo migration of a stent according to the present disclosure, wherein the design of the stent allows for a self-positioning under diastolic pressure.

In some embodiments, multiple fixation elements (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, etc. or 2 to 5, 2 to 10, 2 to 20, 2 to 30, 2 to 40, etc.) may be provided for holding the stent onto a catheter whereas a matching/complimentary element (e.g., stent holder with pins) may be attached to the catheter. The design of the multiple fixation elements (e.g., forming "holes") may allow for the fixation of the stent onto the catheter only when the stent is crimped (see e.g., FIG. 9). The fixation may release automatically when the stent starts to expand. That is, the shape of the stent in the unexpanded state is designed to have holes or free areas that can be used to couple the stent with a stent holder. When the stent is expanded, the expanded configuration is absent suchs holes or free spaces and thus the stent automatically becomes uncoupled or releases from the stent holder upon expansion.

it has been observed in vivo that the design of the stent component allows for self-positioning of the replacement valve under diastolic pressure. Once delivered slightly above the aortic annulus, the stent-valve migrates toward the left ventricle due to the forces caused by the diastolic pressure until it reaches a stable position given by the shape/radial force of the anchoring crown (conically shaped section 2) and the compliance of the aortic annulus (FIG. 13).

For example, with respect to some embodiments of the disclosure, and with reference to FIG. 1A, the stent-valve may be released such that at least a portion of section 102 of the stent component is released at the native valve annulus (e.g., release position). In some preferred embodiments, the release of the stent valve in the release position preferably comprises a full release of the stent valve (i.e., the stent-valve is fully released from the delivery system). Accordingly, subsequent beating of the heart after release results in the stent-valve sliding into a final position, which preferably is the groove formed between stent component sections 102 and 104. The distance between the release position and the final position, which may be in reference to either locations at the implantation site (e.g., within the lumen/heart) and/or locations on the stent component, may comprise a predetermined range, which may include: between about 3 mm and about 20 mm, between about 7 mm to about 11 mm, between about 8 mm to about 12 mm, and between about 9 mm to about 13 mm.

While preferred embodiments are directed toward releasing the stent-valve as described above at a release location on stent component section 102, in still other embodiments, and with reference to FIG. 1A, the stent-valve may be released (which according to some embodiments, is a full release from the stent-valve delivery system) such that at least a portion of section 104 of the stent component is released at the native valve annulus (e.g., release position), and subsequent beating of the heart after release results in the stent-valve sliding into a final position which preferably is the groove portion (as indicated above) between sections 104 and 102. Accordingly, a range of distances between release locations and final positions, which may be in reference to either locations at the implantation site (e.g., within the lumen/heart) and/or locations on the stent component, may be between about 4 mm and 8 mm.

In some embodiments, a valved-sent delivery system, and method for delivering the valved-stent to an implantation site are provided in which the valved-sent is expanded at the implantation site in a stepwise manner (for example) from its distal end towards its proximal end. For example, a release procedure for causing expansion of a valved-stent may involve pulling back a sheath element on a catheter delivery device. The sheath element, in such an embodiment, constrains the valved-sent toward a section of the heart (for example, the left ventricle of the heart). According to such a procedure, there may be no interaction of the delivery system with the anatomy of the ascending aorta/aortic arch. For example, the sheath constraining the valved-stent, and the tip of the delively system may not be required to enter the aortic arch during the release procedure, which is beneficial since such entry potentially can cause a bending moment acting onto the valved-stent and result in inaccurate positioning of the valved-stent (e.g., tilting).

Cardiac Stent Valve Delivery System

Some embodiments of the present disclosure provide a cardiac stent-valve delivery system that includes an inner assembly and an outer assembly. The inner assembly may include a guide wire lumen (e.g., polymeric tubing) and a stent holder for removable attachment to a stent-valve. The outer assembly may include a sheath. The inner member and the outer member may be co-axially positioned and slidable relative to one another in order to transition from a closed position to an open position, such that in the closed position the sheath encompasses the stent-valve still attached to the stent holder and thus constrains expansion of the stent-valve. In the open position, the outer sheath may not constrain expansion of the stent-valve and thus the stent-valve may detach from the stent holder and expand to a fully expanded configuration.

In some embodiments, the inner assembly of the delivery device may include a fluoroscopic marker fixed to the guide wire lumen distal of the stent holder.

In some embodiments, the diameter of the outer assembly of the delivery device varies over its longitudinal axis.

In still other embodiments, the delivery system comprises a rigid (e.g., stainless steel) shaft in communication with a proximal end of the guide wire lumen.

In some embodiments, the delivery system comprises a luer connector m communication with the rigid shaft.

Figure 14A:
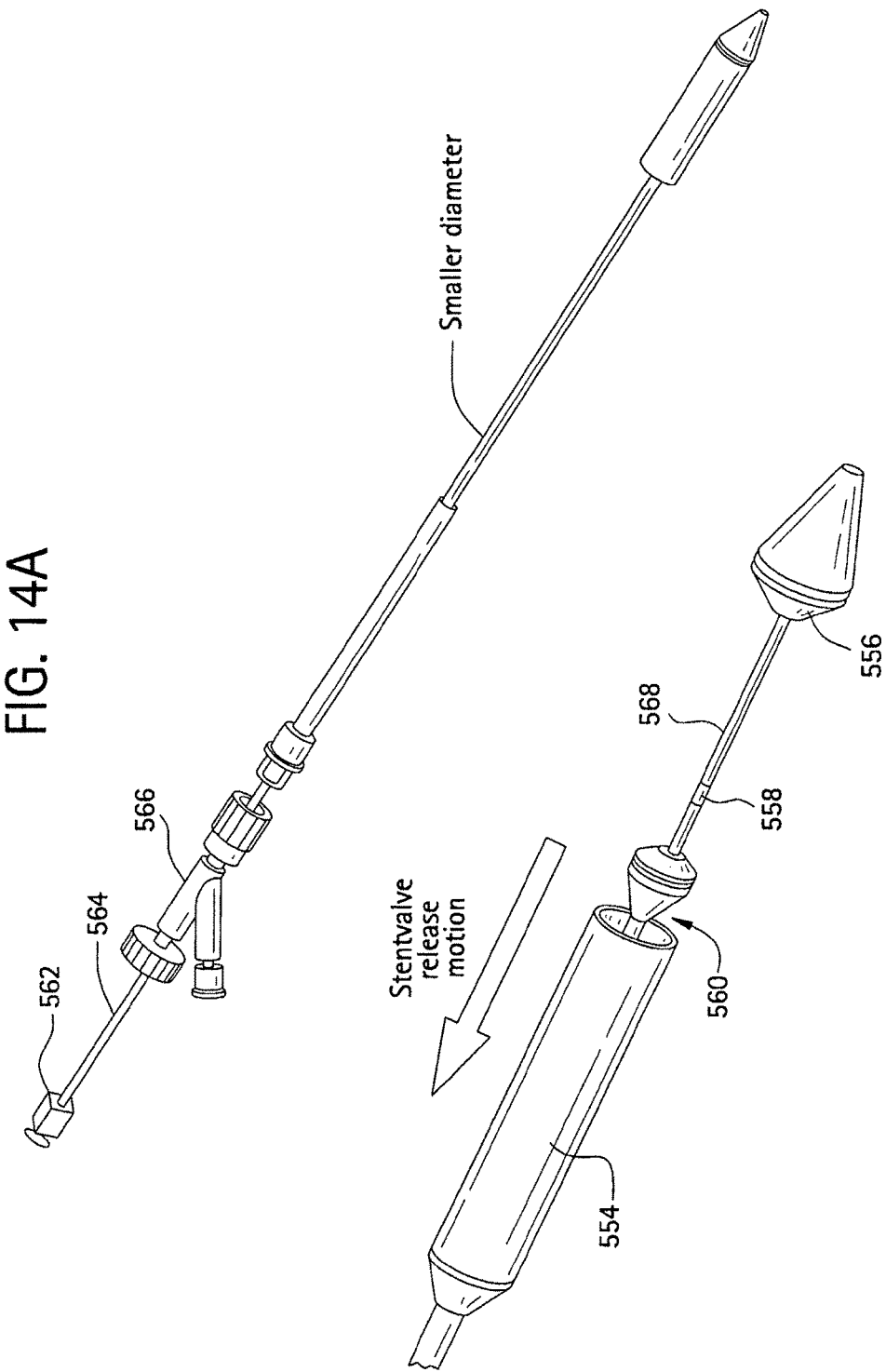
FIG. 14A shows a delivery system for distal-to-proximal expansion of a stent-valve, according to some embodiments of the present disclosure.

FIG. 14A shows a delivery system 550 for distal-to-proximal expansion of a stent-valve (i.e., section 108 to section 102—see FIG. 1), according to some embodiments of the present disclosure. In some embodiments of the delivery system, the system 550 may include an inner member 552 and an outer member 554 (e.g., sheath) which are co-axially positioned and slidable one against the other. The inner member 552 may comprise tubing 568 (e.g., polymeric tubing) which serves as a guide wire lumen and on which at least one of (and preferably several or all) a tip 556, a fluoroscopic marker 558, and a stent-holder 560 are affixed (e.g., bonded). The polymeric tubing may be reinforced proximally with a rigid (e.g., stainless steel) shaft. A luer connector 562 affixed to a stainless steel shaft 564 to allow flushing of the guide wire lumen with saline (for example). The outer member 554 may comprise a distally arranged sheath which may be used to constrain the stent in a closed/contracted (e.g., substantially non-expanded) configuration. Proximally, the sheath may be fixed to a hemostasis valve 566 to allow the flushing of the annular space between the inner and outer members with saline (for example). In some embodiments, the diameter of the outer member may vary over its longitudinal direction (e.g., smaller diameter proximally to decrease the bending stiffness of the delivery system). In some embodiments, the deployment of the stent-valve may occur by holding the inner member at the level of the stainless steel shaft with one hand and the outer member at the level of the hemostasis valve with the other hand. Then, upon positioning of the replacement valve (e.g., under fluoroscopic control), the outer member is pulled back with the inner member being kept at its original position, until the stent is fully deployed.

Figure 14B:
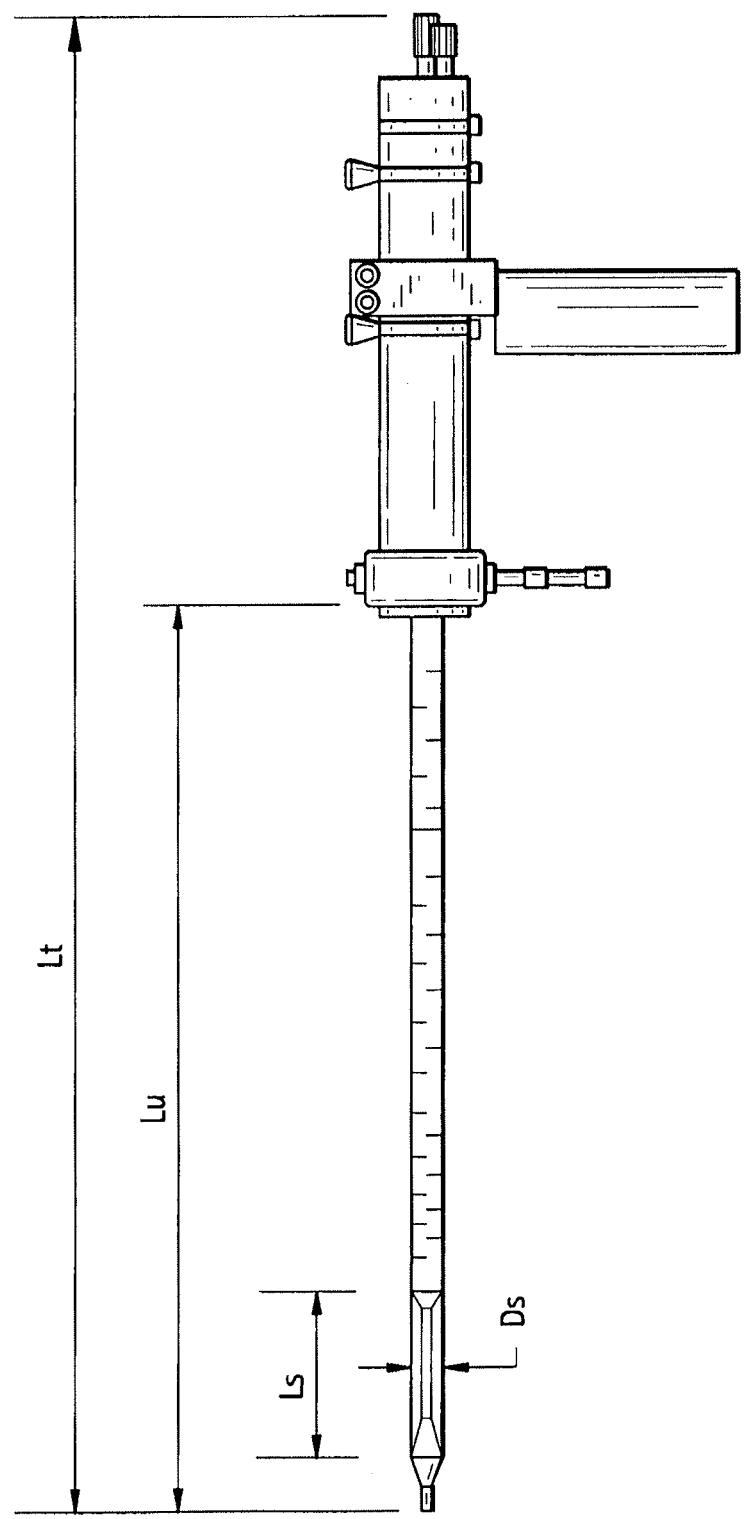
FIG. 14B shows the size and shape of delivery system according to some embodiments.

FIG. 14B shows the size and shape of delivery system according to some embodiments. Ds refers to the stent sleeve diameters, which are the inner and outer sleeve diameters. The inner diameter of the stent sleeve is preferably from between about 4 to about 14 mm (e.g., about 4 mm, 5 mm, 6 mm, 7 mm, 8 mm, 9 mm, 10 mm, 11 mm, 12 mm, 13 mm, or 14 mm). The outer diameter of the stent sleeve is preferably from between about 5 to about 15 mm (e.g., about 5 mm, 6 mm, 7 mm, 8 mm, 9 mm, 10 mm, 11 mm, 12 mm, 13 mm, 14 mm, or 15 mm).

Ls refers to the stent sleeve length. The stent sleeve length is preferably from between about 20 mm to about 120 mm (e.g., about 20 mm, 25 mm, 30 mm, 35 mm, 40 mm, 50 mm, 60 mm, 70 mm, 80 mm, 90 mm, 100 mm, 110 mm, or 120 mm). According to some embodiments, the stent sleeve length is between from about 20 mm to about 100 mm, about 20 mm to about 80 mm, about 20 mm to about 60 mm, about 20 111 m to about 40 mm, about 40 mm to about 120 mm, about 60 mm to about 120 mm, about 80 mm to about 120 mm, about 100 mm to about 120 mm, about 40 mm to about 100 mm, or about 60 mm to about 100 mm.

Lu refers to the usable length. The usable length is preferably from between about 150 mm to about 500 mm (e.g., about 150 mm, 175 mm, 200 111 m, 225 mm, 250 mm, 300 mm, 350 mm, 400 mm, 450 mm, or 500 mm). According to some embodiments, the usable length is between from about 150 mm to about 450 mm, about 150 mm to about 400 mm, about 150 mm to about 350 mm, about 150 mm to about 300 mm, about 150 mm to about 250 mm, about 200 mm to about 500 mm, about 300 mm to about 500 mm, about 350 mm to about 500 mm, about 400 mm to about 500 mm, about 200 mm to about 400 mm, or about 300 mm to about 400 mm.

Lt refers to the total length. The total length is preferably from between about 200 mm to about 1000 mm (e.g., about 200 mm, 225 mm, 250 mm, 300 mm, 350 mm, 400 mm, 450 mm, 500 mm, 550 mm, 600 mm, 650 mm, 700 mm, 750 mm, 800 mm, 850 mm, 900 mm, 950 mm, or 1000 mm). According to some embodiments, the total length is between from about 200 mm to about 900 mm, about 200 mm to about 800 mm, about 200 mm to about 700 mm, about 200 mm to about 600 mm, about 200 mm to about 500 mm, about 200 mm to about 400 mm, about 200 mm to about 300 mm, about 300 mm to about 1000 mm, about 400 mm to about 1000 mm, about 500 mm to about 1000 mm, about 600 mm to about 1000 mm, about 700 mm to about 1000 mm, about 800 mm to about 1000 mm, about 900 mm to about 1000 mm, or about 300 mm to about 800 mm.

Figure 15A:
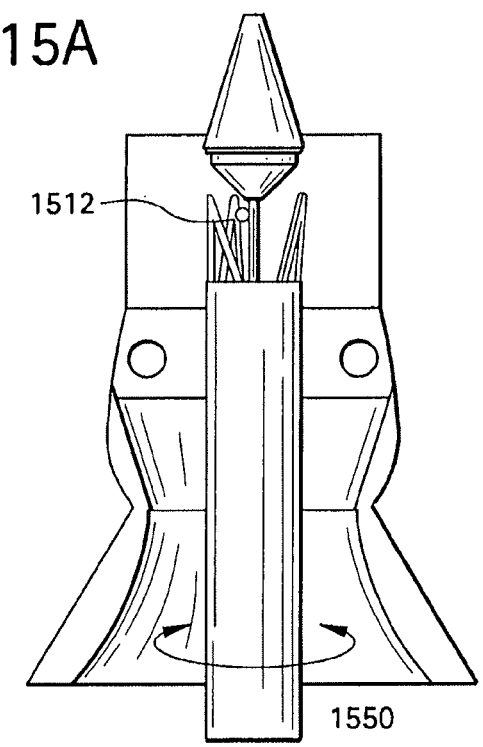
FIGS. 15A-D illustrate a method of implanting a stent-valve within a human heart according to some embodiments of the present disclosure.

FIGS. 15A-D illustrate an exemplary embodiment of a method of implanting a stent-valve within a human heart according to some embodiments of the present disclosure (e.g., an aortic valve replacement). Accordingly, FIG. 15A shows the initial, partial release of the stent 1500, in which the radiopaque 1512 marker positioned on one of the arches of stent section 1508 (see FIG. 1), for example, is released distally from the outer sheath . By tracking the radiopaque marker 1512, the delivery system 1550 may then be rotated as necessary in order to orient the stent 1500 appropriately with respect to, for example, the coronary arteries (e.g., orienting the stent-valve such that the commissures do not face the coronary arteries). More specifically, prior to full release of the stent 1500, the delivery system 1550 may be rotated in order to cause the radiopaque marker 1512 to be placed between the osteum of the left and right coronary arteries.

Figure 15B:
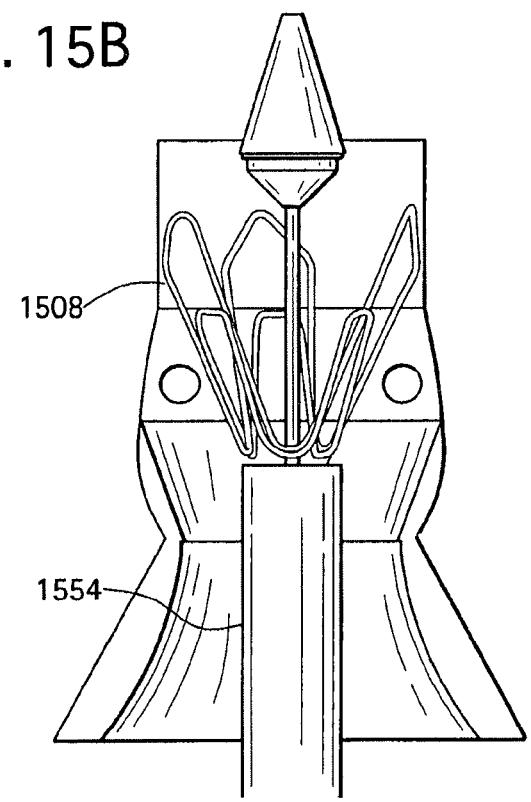

FIG. 15B shows a further, but still partial release of the stent 1500, in which the larger, orientation arches 1509 of stent section 1508 are released from the outer sheath 1554 and placed into contact with the aorta (for example).

Figure 15C:
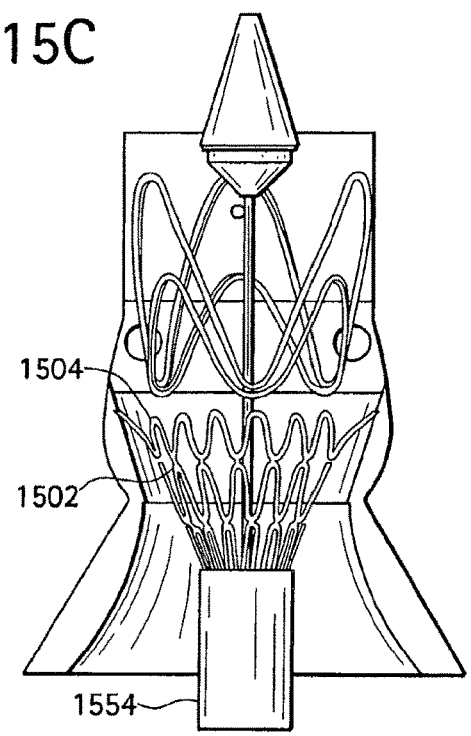

FIG. 15C illustrates an example of yet a further, still partial release but almost fully released, illustration of the stent release, in which the first conical crown of stent section 1504 is released from the outer sheath 1554 for engagement with the native valve leaflets 1580.

Figure 15D:
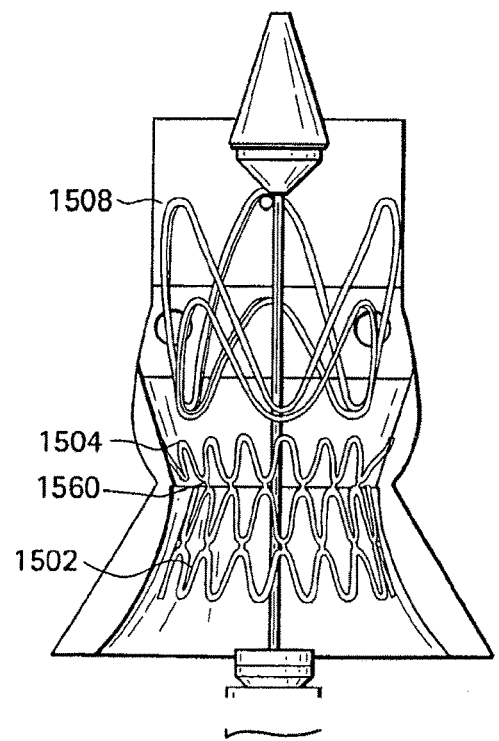
Figure 16A:
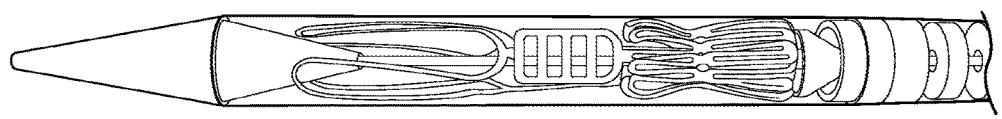
FIGS. 16A-D illustrate the partial release of a stent according to the present disclosure, the release of which is stopped by a security tab.
Figure 16B:
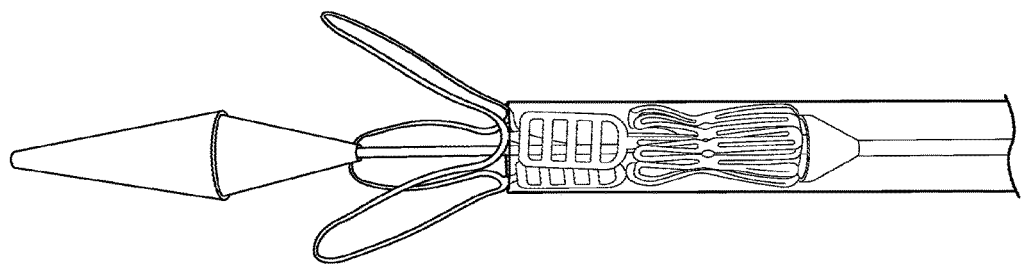
Figure 16C:
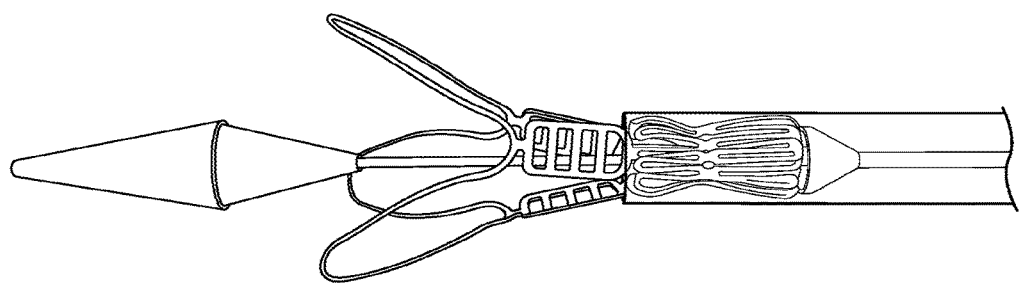
Figure 16D:
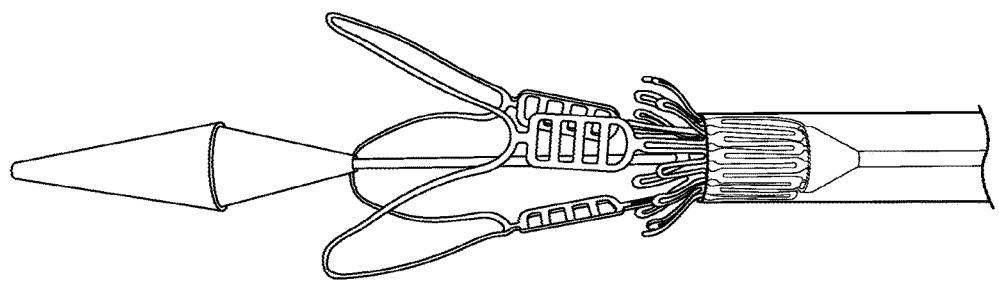
Figure 17A:
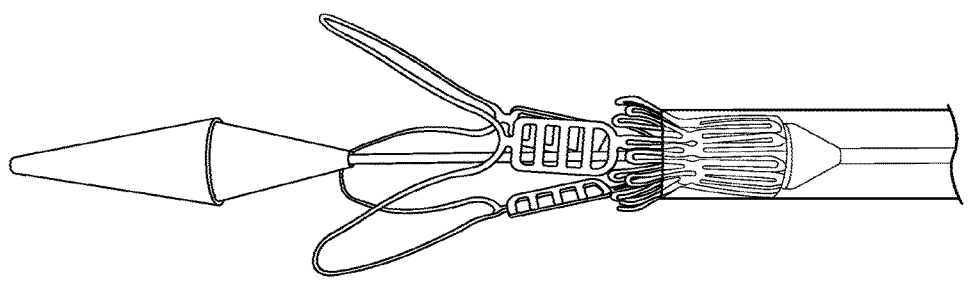
FIGS. 17A-D illustrate the capture of the stent after partial release according to FIG. 16.
Figure 17B:
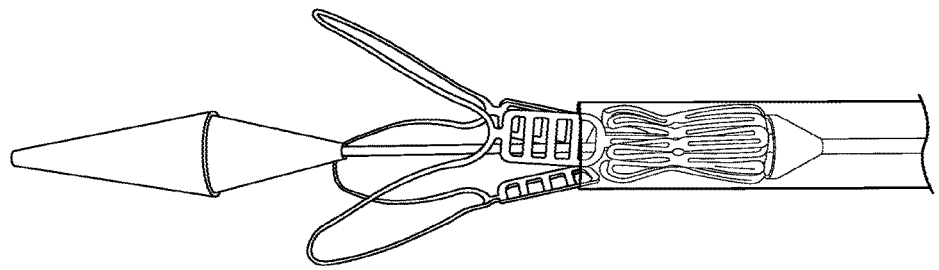
Figure 17C:
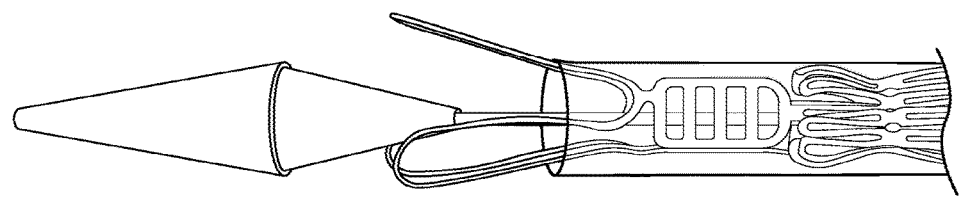
Figure 17D:
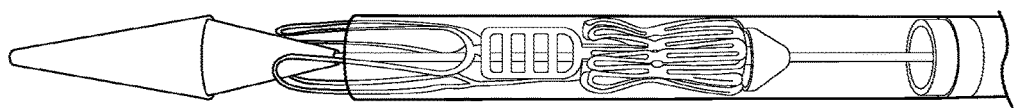

FIG. 15D illustrates an example of a full release of the stent, in which the second conical crown of stent section 1502 (i.e., the proximal section of the stent; see FIG. 1) is released from the outer sheath 1554 for engagement with the annulus/inflow tract.

Medical Uses

According to some embodiments, cardiac stent-valves are provided as cardiac replacement valves. There are four valves in the heart that serve to direct the flow of blood through the two sides of the heart in a forward direction. On the left (systemic) side of the heart are: 1) the mitral valve, located between the left atrium and the left ventricle, and 2) the aortic valve, located between the left ventricle and the aorta. These two valves direct oxygenated blood coming from the lungs through the left side of the heart into the aorta for distribution to the body. On the right (pulmonary) side of the heart are: 1) the tricuspid valve, located between the right atrium and the right ventricle, and 2) the pulmonary valve, located between the right ventricle and the pulmonary artery. These two valves direct de-oxygenated blood coming from the body through the right side of the heart into the pulmonary artery for distribution to the lungs, where it again becomes re-oxygenated to begin the circuit anew.

Problems that can develop with heart valves consist of stenosis, in which a valve does not open properly, and/or insufficiency, also called regurgitation, in which a valve does not close properly. In addition to stenosis and insufficiency of heart valves, heart valves may need to be surgically repaired or replaced due to certain types of bacterial or fungal infections in which the valve may continue to function normally, but nevertheless harbors an overgrowth of bacteria on the leaflets of the valve that may embolize and lodge downstream in a vital artery. In such cases, surgical replacement of either the mitral or aortic valve (left-sided heart valves) may be necessary. Likewise, bacterial or fungal growth on the tricuspid valve may embolize to the lungs resulting in a lung abscess. In such cases replacement of the tricuspid valve even though no tricuspid valve stenosis or insufficiency is present.

According to some embodiments, there is provided a method for replacing a worn or diseased valve comprising transapically implanting a replacement valve, wherein the replacement valve is a stent-valve of the present disclosure. Accordingly, the replacement valve comprises a valve component and a stent component, wherein the valve component is connect to the stent component.

The stent component preferably comprises a longitudinal axis and preferably has four sections. The first section, as above, includes a substantially conical shape having a narrow end, a broad end and a predetermined first height. The second section, as above, includes a substantially conical shape having a narrow end, a broad end and a predetermined second height. The center of each of the first section and the second section are preferably arranged to align substantially with the longitudinal axis. The narrow ends of the first section and second section are preferably arranged to meet forming an annular groove to receive the annulus of worn or diseased cardiac valve at an implantation site of the heart.

The first height of the first section is preferably greater than the second height of the second section. Upon implantation, the replacement valve is positioned so that the annular groove receives the annulus of the worn or diseased cardiac valve.

As the stent-valves of the present disclosure are designed to be self-positioning under diastolic pressure (i.e., permissible in vivo migration), the placement of the stent-valve may be upstream of the annulus, whereupon when the stent-valve will be locked into position once the annular groove of the stent component receives the annulus. Thus, according to some embodiments, methods are provided for implanting a replacement valve into a heart of a mammal comprising delivering a replacement valve to an implantation site of the heart of the mammal. The implantation site preferably comprises a release location and a final location; and the release location is spaced apart from the final location (and according to some embodiments, the spacing comprises a predetermined distance), and in some embodiments, in a blood upflow direction. Releasing t h e replacement valve at the release location, the replacement valve is able to slide into the final location, generally upon at least one beat of the heart subsequent to the replacement valve being released at the release location.

According to some embodiments, the methods provides that when the replacement valve sliding into the final location, the replacement valve is substantially positioned to the final location.

In some embodiments of the present disclosure, a method is provided for replacing an aortic valve within a human body. A stent-valve may be covered with a sheath in order to maintain the stent-valve in a collapsed configuration. The stent-valve may then may be inserted in the collapsed configuration into the human body without contacting the ascending aorta or aortic arch. The stent-valve may be partially expanded by sliding the sheath towards the left ventricle of the heart. This sliding of the sheath towards the left ventricle may cause expansion of a distal end of the stent-valve while the proximal end of the stent-valve remains constrained by the sheath. The sheath may be further slid towards the left ventricle of the heart in order to cause full expansion of the stent-valve. In some embodiments, the stent-valve may be recaptured prior to its full expansion by sliding the sheath in the opposite direction.

In some embodiments, a method for cardiac valve replacement is provided that includes releasing a distal end of a stent-valve from a sheath, where the distal end includes a radiopaque marker positioned thereon. The stent-valve is rotated, if necessary, to orient the stent-valve appropriately with respect to the coronary arteries (e.g., to prevent the commissures from facing the coronary arteries). Arches of the stent-valve are released from the sheath, in order to cause the arches to contact the aorta. A first conical crown of the stent-valve is released from the sheath, in order to cause the first conical crown to contact the native valve leaflets. A second crown of the stent-valve is released from the sheath, in order to cause the second crown to contact an annulus/inflow tract. The second crown may be the proximal section of the stent-valve such that releasing the second crown causes the stent-valve to be fully released from the sheath.

According to some embodiments, a replacement valve for use within a human body is provided, where the replacement valve includes a valve component and a stent component. The stent component also may be used without a connected valve as a stent. The stent devices of the present disclosure may use used to mechanically widen a narrowed or totally obstructed blood vessel; typically as a result of atherosclerosis. Accordingly, the stent devices of the present disclosure may use used is angioplasty procedures. These include: percutaneous coronary intervention (PCI), commonly known as coronary angioplasty, to treat the stenotic (narrowed) coronary arteries of the heart found in coronary heart disease; peripheral angioplasty, performed to mechanically widen the opening in blood vessels other than the coronary arteries.

Thus, it is seen that stent-valves (e.g., single-stent-valves and double-stent-valves) and associated methods and systems for surgery are provided. Although particular embodiments have been disclosed herein in detail, this has been done by way of example for purposes of illustration only, and is not intended to be limiting with respect to the scope of the appended claims, which follow. In particular, it is contemplated by the applicant that various substitutions, alterations, and modifications may be made without departing from the spirit and scope of invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

What is claimed is:

1. A delivery system, comprising:
   a catheter shaft;
   a prosthetic valve coupled to the catheter shaft, the prosthetic valve including a stent and a plurality of leaflets coupled to the stent;
   wherein the stent has an inflow end region and an outflow end region;
   a sealing member coupled to the inflow end region; and
   one or more fixation elements disposed along the stent, the one or more fixation elements being designed to releasably secure the stent to the catheter shaft,
   wherein the sealing member includes a polymer.

2. A delivery system, comprising:
   a catheter shaft;
   a prosthetic valve coupled to the catheter shaft, the prosthetic valve including a stent and a plurality of leaflets coupled to the stent;
   wherein the stent has an inflow end region and an outflow end region;
   a sealing member coupled to the inflow end region; and
   one or more fixation elements disposed along the stent, the one or more fixation elements being designed to releasably secure the stent to the catheter shaft,
   wherein the sealing member includes a fabric skirt.

3. A delivery system, comprising:
   a delivery catheter including a catheter shaft;
   a handle coupled to the catheter shaft;
   a prosthetic valve coupled to the catheter shaft, the prosthetic valve including a stent and a plurality of leaflets coupled to the stent;
   wherein the stent has an inflow end region, an outflow end region, and a central region disposed between the inflow end region and the outflow end region;
   wherein the inflow end region has an inflow outer diameter;
   wherein the outflow end region has an outflow outer diameter;
   wherein the central region has a central outer diameter;
   wherein the inflow outer diameter, the outflow outer diameter, or both are greater than the central outer diameter;
   a sealing member coupled to the inflow end region; and a fixation element disposed along the stent, the fixation element being designed to releasably secure the stent to the catheter shaft.

4. The delivery system of claim 1, wherein the sealing member is an inner skirt.

5. The delivery system of claim 1, wherein the stent includes a reverse anchoring crown comprising a plurality of proximal tips interspersed between successive fixation elements.

6. The delivery system of claim 5, wherein the plurality of proximal tips comprises four proximal tips.

7. The delivery system of claim 1, wherein the inflow end region, the outflow end region, or both are flared.

8. The delivery system of claim 1, wherein the inflow end region has an inflow outer diameter,
wherein the outflow end region has an outflow outer diameter, and
the inflow outer diameter is different from the outflow outer diameter.

9. The delivery system of claim 8, wherein the stent has a central region disposed between the inflow end region and the outflow end region, and wherein the central region has a central outer diameter that is smaller than the inflow outer diameter, the outflow outer diameter, or both.

10. The delivery system of claim 1, wherein the one or more fixation elements secure the stent to the catheter shaft when the stent is in a collapsed configuration and wherein the one or more fixation elements are released from the catheter shaft when the stent shifts to an expanded configuration.

11. The delivery system of claim 2, wherein the sealing member is an inner skirt.

12. The delivery system of claim 2, wherein the stent includes a reverse anchoring crown comprising a plurality of proximal tips interspersed between successive fixation elements.

13. The delivery system of claim 12, wherein the plurality of proximal tips comprises four proximal tips.

14. The delivery system of claim 12, wherein the inflow end region, the outflow end region, or both are flared.

15. The delivery system of claim 12, wherein the inflow end region has an inflow outer diameter,
wherein the outflow end region has an outflow outer diameter, and
the inflow outer diameter is different from the outflow outer diameter.

16. The delivery system of claim 15, wherein the stent has a central region disposed between the inflow end region and the outflow end region, and wherein the central region has a central outer diameter that is smaller than the inflow outer diameter, the outflow outer diameter, or both.

17. The delivery system of claim 2, wherein the one or more fixation elements secure the stent to the catheter shaft when the stent is in a collapsed configuration and wherein the one or more fixation elements are released from the catheter shaft when the stent shifts to an expanded configuration.

* * * * *